(12) United States Patent
Herbst et al.

(10) Patent No.: US 10,943,243 B2
(45) Date of Patent: Mar. 9, 2021

(54) ELECTRONIC SYSTEM TO ROMANTICALLY MATCH PEOPLE BY COLLECTING INPUT FROM THIRD PARTIES

(71) Applicant: Social Data Sciences, Inc., Arlington, VA (US)

(72) Inventors: Daniel C. Herbst, Arlington, VA (US); Sean P. Finegan, Los Angeles, CA (US)

(73) Assignee: Social Data Sciences, Inc.

( * ) Notice: Subject to any disclaimer, the term of this patent is extended or adjusted under 35 U.S.C. 154(b) by 13 days.

(21) Appl. No.: 15/476,953

(22) Filed: Mar. 31, 2017

(65) Prior Publication Data

US 2017/0300935 A1  Oct. 19, 2017

Related U.S. Application Data

(63) Continuation-in-part of application No. 15/447,527, filed on Mar. 2, 2017, now Pat. No. 10,051,814.

(60) Provisional application No. 62/316,824, filed on Apr. 1, 2016, provisional application No. 62/302,340, filed on Mar. 2, 2016, provisional application No. 62/401,170, filed on Sep. 29, 2016.

(51) Int. Cl.
| | |
|---|---|
| *G06F 17/00* | (2019.01) |
| *G06Q 30/02* | (2012.01) |
| *A61B 5/16* | (2006.01) |
| *G06Q 50/00* | (2012.01) |
| *G06Q 50/10* | (2012.01) |
| *G06F 16/00* | (2019.01) |

(52) U.S. Cl.
CPC ......... *G06Q 30/0201* (2013.01); *A61B 5/167* (2013.01); *G06F 16/00* (2019.01); *G06Q 50/01* (2013.01); *G06Q 50/10* (2013.01); *G06Q 30/02* (2013.01)

(58) Field of Classification Search
CPC .... G06Q 30/0201; G06Q 50/01; G06Q 50/10; G06Q 30/02; G06F 16/00; A61B 5/167
See application file for complete search history.

(56) References Cited

U.S. PATENT DOCUMENTS

| | | | | |
|---|---|---|---|---|
| 2004/0143841 | A1* | 7/2004 | Wang | G06Q 30/02 725/32 |
| 2006/0041586 | A1* | 2/2006 | Nassef | G06F 17/30867 |
| 2006/0106780 | A1* | 5/2006 | Dagan | G06Q 10/107 |
| 2007/0288546 | A1* | 12/2007 | Rosenberg | G06Q 10/10 709/201 |
| 2008/0077517 | A1* | 3/2008 | Sappington | G06Q 30/02 705/35 |
| 2008/0147743 | A1* | 6/2008 | Taylor | G06Q 30/02 |

(Continued)

*Primary Examiner* — Syed H Hasan
(74) *Attorney, Agent, or Firm* — Pacifica IP

(57) ABSTRACT

Methods and apparatus for a social-oriented computer system for matching daters. Daters establish friend connections with other users, including non-daters. After identifying candidate pairings of daters, the system solicits the opinions of users including the daters, their friends, and matchmakers. The system may analyze the opinions to determine whether a match would result in the satisfaction of both daters. If so, the system matches the daters, inviting them to communicate. The system may gather feedback on the match to help calibrate future matching.

6 Claims, 8 Drawing Sheets

(56) References Cited

U.S. PATENT DOCUMENTS

| | | | | |
|---|---|---|---|---|
| 2008/0270038 A1* | 10/2008 | Partovi | ................ | G06Q 10/00 |
| | | | | 702/19 |
| 2009/0070684 A1* | 3/2009 | Aldrich | ................ | G06Q 50/01 |
| | | | | 715/743 |
| 2009/0094048 A1* | 4/2009 | Wallace | ................ | G06Q 30/02 |
| | | | | 705/319 |
| 2014/0040365 A1* | 2/2014 | Carter | ................ | H04L 67/22 |
| | | | | 709/204 |
| 2014/0172893 A1* | 6/2014 | Carter | ................ | G06F 16/337 |
| | | | | 707/758 |
| 2015/0127638 A1* | 5/2015 | Parks | ................ | G06F 17/3087 |
| | | | | 707/723 |
| 2015/0150100 A1* | 5/2015 | Soni | ................ | H04L 63/0876 |
| | | | | 726/7 |
| 2018/0130139 A1* | 5/2018 | Hurley | ................ | G06Q 50/01 |

* cited by examiner

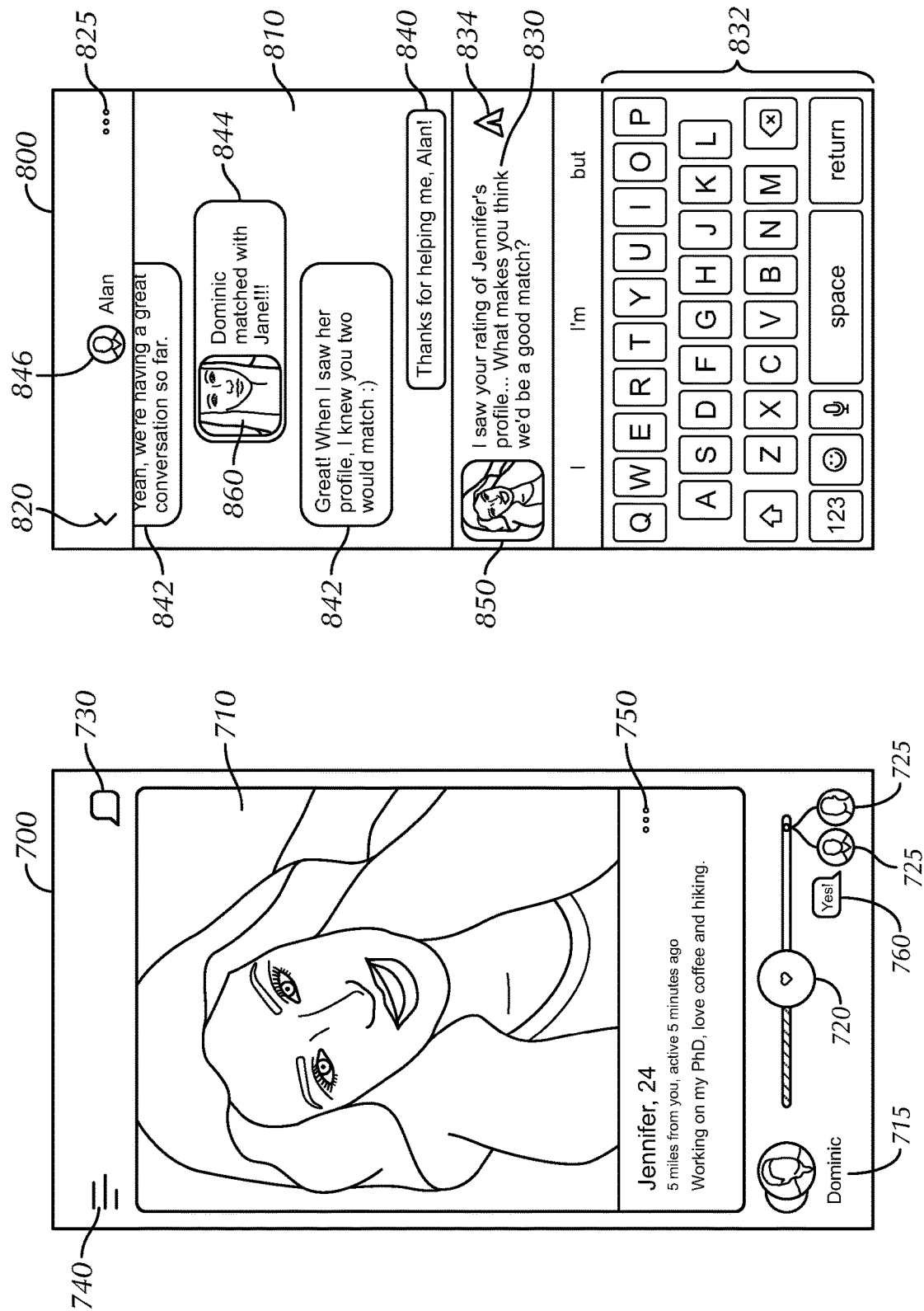

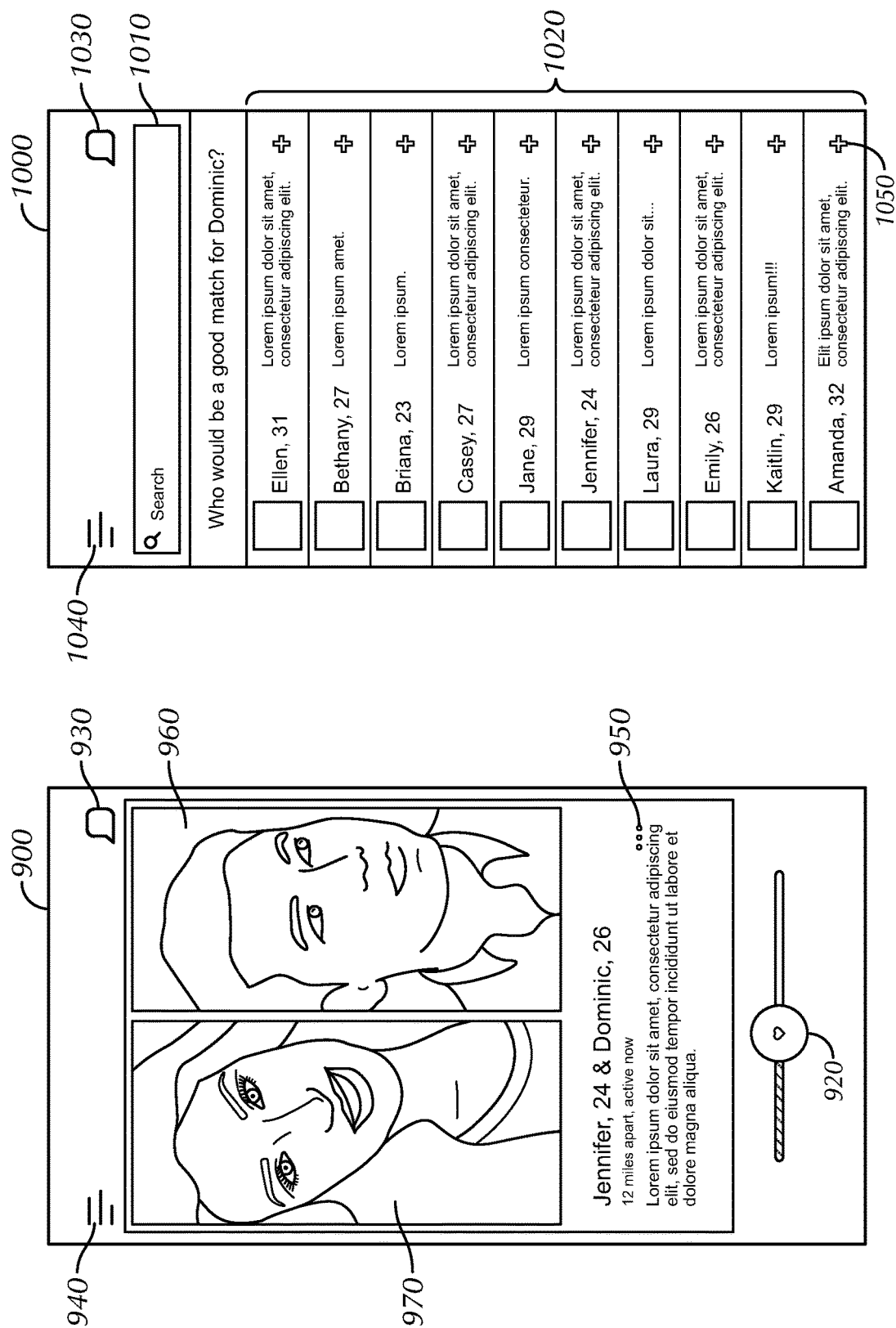

ELECTRONIC SYSTEM TO ROMANTICALLY MATCH PEOPLE BY COLLECTING INPUT FROM THIRD PARTIES

CROSS-REFERENCE TO RELATED APPLICATIONS

This application claims priority under 35 U.S.C. § 119(e) from co-pending U.S. Provisional Patent Application No. 62/316,824, by Sean P. Finegan and Daniel C. Herbst, "Electronic Dating System" filed Apr., 1, 2016, and is a continuation-in-part of U.S. patent application Ser. No. 15/447,527 filed Mar. 2, 2017, which claims priority under 35 U.S.C. § 119(e) from U.S. Provisional Patent Application No. 62/302,340, "A System to Customize Recommendations by Soliciting and Analyzing Suggestions and Evaluations Tailored to a Particular Subject" by Sean P. Finegan and Daniel C. Herbst, "Electronic Recommendation System" filed Mar. 2, 2016, and Provisional Patent Application No. 62/401,170, by Sean P. Finegan and Daniel C. Herbst, "Electronic Evaluation System" filed Sep. 29, 2016, which, by this statement, are incorporated herein by reference for all purposes.

FIELD OF THE INVENTION

The present invention relates to an electronic dating system, and more particularly provides methods and apparatus for a user to evaluate potential pairings between users, which may possibly include him or herself.

BACKGROUND OF THE INVENTION

As social networking applications have become more popular with the continued development of the internet, electronic dating systems have experienced a surge of growth. A dating system is any system that uses a computer to connect a person with a romantic partner. Many of these systems attempt to do this by presenting users with a series of potential partners. Users may be given the chance to evaluate the potential partners they have been presented with, as well as given a way to pursue further interaction.

However, existing electronic dating systems have shortcomings. First, with no peer involvement, the average user's autobiographical information is commonly known to suffer from self-reporting biases, as well as exaggeration, selective inclusion or exclusion of detail, and/or outright falsehood. Second, there are often many profiles to sift through. A common advantage of many dating systems is their access to a larger pool of potential partners than the average user would encounter in everyday life. However, it is difficult to pare down the list of potential partners beyond simple, objective criteria like age, distance, gender, etc. As a result, a user may be overwhelmed.

Third, a user may not trust the recommendations of a computer algorithm. Even the best algorithms struggle to understand the needs and wants of humans; more fundamentally, algorithms do not have a personality. Fourth, existing dating systems can be a solitary experience for a user, since the vast majority of the user's interaction is with potential partners, who are effectively strangers. Fifth, most dating systems cater exclusively to users looking for partners, and do not have a role for "non-dating" users. Among other things, this means that a user who is able to find a partner may feel the need to delete or deactivate the system. Should the user have use for the system at a later date, they will have to go through the cumbersome process of redownloading it, and may potentially have to start anew. Moreover, this is harmful from a business perspective, since a successful match means a lost customer: a user in a relationship is excluded from using the application.

Most of all, existing dating systems tend not to capture the positive aspects of traditional real-life dating, which include the consultation of trusted friends and/or advice-givers as well as properly contextualized evaluations. In addition, the digital age has eroded many of these aspects. Modern friend groups tend to be spread out and people may have busy schedules. Geography, timing, limited information, and a number of other challenges make it impossible for a person in real life to consult all of the people he or she would want to, let alone gather feedback from them and consider it in a way that is useful in decision-making.

In light of the foregoing discussion, there is need for a dating system that presents solutions to these problems at the same time that it builds on the positive aspects of real-life dating.

BRIEF SUMMARY OF THE INVENTION

The present system uses a collection of automated subsystems and associated databases that work in combination with input from one or more users to romantically match people. In the preferred embodiment, the system allows users to establish friend connections with other users. A friend connection allows a user to take a special role in the partner selection process of the user's friend. This has many advantages. Friends may offer one another advice and support, which adds a collaborative, social component to the dating process. The involvement of friends also encourages users to provide accurate autobiographical information, since they know their friends may see their profile. Additionally, a person is an excellent resource for the system when it comes to a friend's likes, dislikes, personality, and general insight into their life.

In the preferred embodiment, users can opt to be daters or non-daters at will. A dater is a user seeking a romantic partner. A non-dater is a user not seeking a romantic partner. Daters construct public profiles that include autobiographical information and photographs. Daters also specify basic filtering criteria for a partner, such as gender, age, and distance. By clearly delineating roles for daters and non-daters, the system allows non-daters to use the application without stigma, and become involved in the dating life of their single friends.

In the preferred embodiment, the system identifies quality matches between daters in a two-stage process. First, the system performs a simple database search using the dater-specified basic filtering criteria to identify candidate pairings of daters. Next, the system selects evaluators from amongst the dater and the dater's friends, to evaluate the other dater in the pairing. Both daters and non-daters may evaluate romantic pairings. In the preferred embodiment, types of evaluations include a binary yes/no suggesting feature, written evaluations that the dater can reference, and numeric ratings that are easily interpretable by the computer system. In addition, the preferred embodiment introduces an additional user role, matchmaker, that allows such a user to rate the pairing itself. Therefore, likely quality pairings can be identified without overwhelming the daters involved, because friends can weed out any particularly poor pairings.

In the preferred embodiment, the system uses a probabilistic processing feature to identify quality pairings based on the collection of ratings received regarding each pairing. It makes use of prior rating behavior of users, with the goal of amplifying accurate evaluators. This feature produces better decisions with fewer ratings required.

The system issues a Match for a pairing that is likely to result in satisfaction for both daters. A Match is a formal introduction of the two daters, allowing them to communicate. An outcome is defined as any success or failure between the daters after they have been issued a Match, including mutual satisfaction or lack thereof, whether or not they went on a date, formed a relationship, etc. In the preferred embodiment, the notification of a Match is accompanied by a system-generated report highlighting the reason for the Match. The report contains ratings and evaluations from friends, so a dater trusts the system and is hopefully encouraged by consensus from friends.

The delineation of roles allows the system to accommodate users who would not normally use this kind of system. For example, after a dater enter into a successful relationship, that dater may continue to participate in the process as a non-dater, helping friends find love, too. This is tremendously helpful from a business perspective since it promotes user retention.

Other features and advantages of the present invention will become apparent from the following more detailed description, taken in conjunction with the accompanying drawings, which illustrate, by way of example, the principles of the invention.

BRIEF DESCRIPTION OF THE FIGURES

FIG. 7 illustrates an example of an evaluation page of a client interface of an embodiment;

FIG. 8 illustrates an example of a chat page of a client interface of an embodiment;

FIG. 9 illustrates an example of a matchmaker's evaluation page of a client interface of an embodiment;

FIG. 10 illustrates an example of a suggesting page of a client interface of an embodiment.

DETAILED DESCRIPTION OF THE INVENTION

Figure 1:
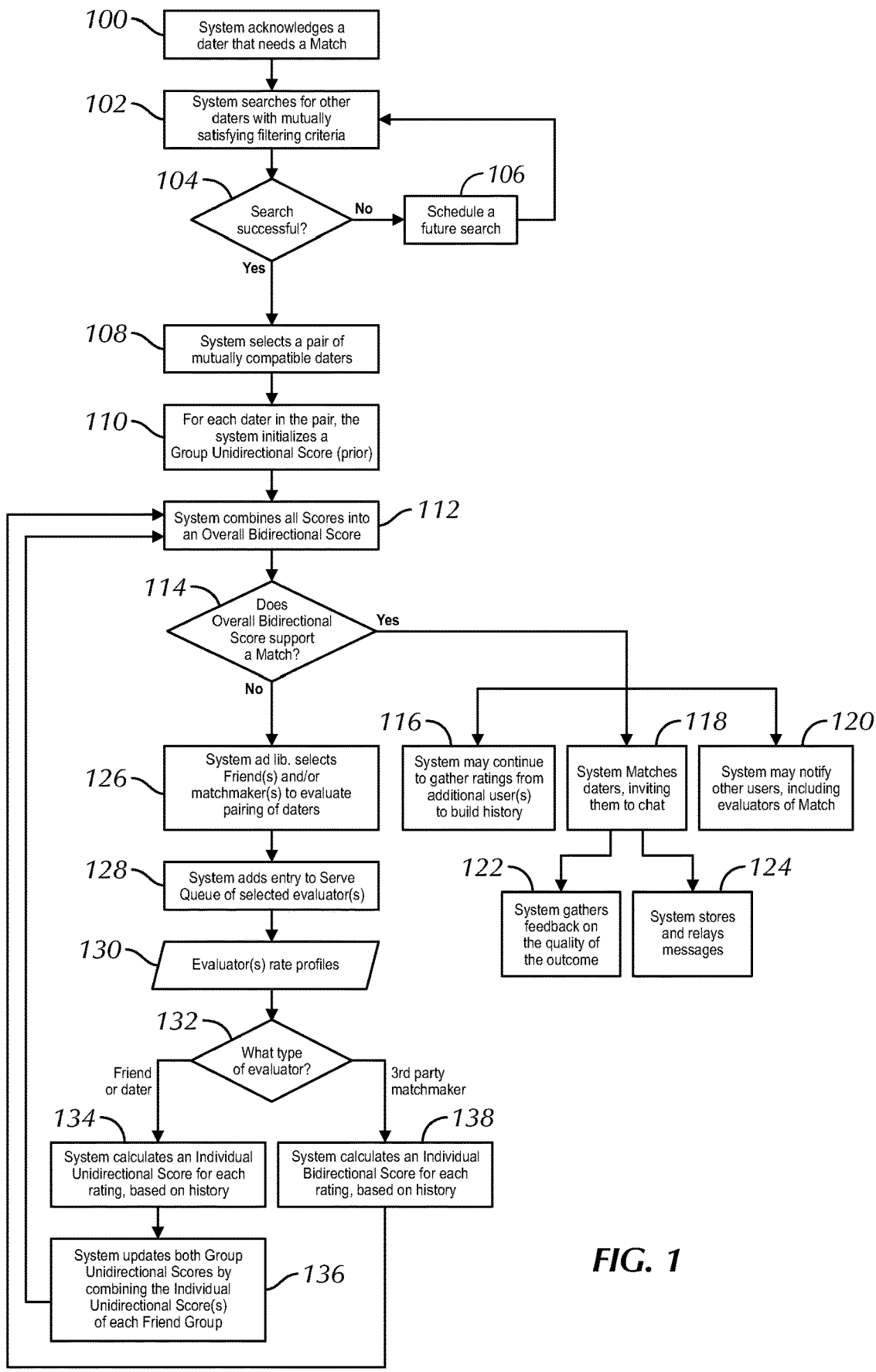
FIG. 1 illustrates the overall flow of events contributing to a single Match between two daters.

The following describes specific example embodiments of the present invention, with reference to the accompanying drawings wherein like numerals refer to like or corresponding elements throughout. This invention, however, may be embodied in many different ways, and the description and drawings related thereto should not be construed as limiting in any sense. Rather, the intention is to cover all modifications, equivalents, and alternatives falling within the spirit and scope of the present invention.

As will be appreciated by one skilled in the art, aspects of the present invention may be embodied as a system, method, device, or a computer program product. Accordingly, the present invention may take the form of an entirely software embodiment, or an embodiment that combines hardware and software aspects.

The flow diagrams in accordance with exemplary embodiments of the present invention are provided as examples and should not be construed to limit other embodiments within the scope of the invention. For instance, the blocks should not be construed as steps that must proceed in a particular order. Additional blocks/steps may be added, some blocks/steps removed, or the order of the blocks/steps altered and still be within the scope of the invention. Further, blocks within different figures can be added to or exchanged with other blocks in other figures. Further yet, specific numerical data values (such as specific quantities, numbers, categories, etc.) or other specific information should be interpreted as illustrative for discussing exemplary embodiments. Such specific information is not provided to limit the invention.

This document makes reference to multiple embodiments of the present invention. The phrases "in one embodiment," and "in an embodiment," as used herein do not necessarily refer to the same embodiment, although they may. In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Some embodiments may use some or all of the following terminology. The meanings of these terms are not limited by the following definitions, and may be expanded or narrowed depending on the embodiment, as described throughout the document. The system is the collection of all software and hardware in an embodiment. A user is a person or entity that interacts with the system.

The preferred embodiment revolves around the formation of romantic relationships. A dater is a user who wants to be introduced to one or more people in a romantic context, with the hope of forming some degree of romantic relationship. A non-dater is a user who does not want to be considered for this kind of introduction. Non-daters are, by definition, not daters. A user may be one or the other, but not both at the same time. In the preferred embodiment, a dater may switch at will between being a dater and non-dater. In other embodiments, this distinction is made by the system. In other embodiments, this distinction is made by other users, and/or a combination of the aforementioned and other means.

Both daters and non-daters may serve in the role of evaluator. An evaluator is an entity that provides an opinion on a dater on behalf of another dater, or an opinion on the compatibility of a pair of daters being considered for a Match. In the preferred embodiment, users serve as evaluators, and the system may also serve as an evaluator. An evaluation is the opinion expressed by an evaluator. Examples of evaluations include written statements, numerical ratings, and opinions recorded by audio or video. An evaluator who provides an opinion on a pair of daters, without representing one dater specifically, is called a matchmaker. A matchmaker evaluates the mutual compatibility of a pairing, that is, considering bother daters' likely satisfaction with being paired with the other. A rating is a type of evaluation, one that corresponds to a numeric rating. A rater is an evaluator that provides a rating. A rating is a type of evaluation, one that corresponds to a numeric rating. A rater is an evaluator that provides a rating.

Friendship is a mutually agreed-upon status between two users. In one embodiment, Friendship implies that one user is rating for the other user. in certain embodiments, Friends may communicate through various means. In the preferred embodiment, Friends may rate on behalf of any dater they are Friends with. Each dater has one Friend Group, defined as the Friends evaluating on behalf of that dater, and also including the dater.

In certain embodiments, a Match is the introduction by the system of one dater to one or more other people. In the preferred embodiment, a Match is made between two daters. Other embodiments include Matches that involve more than two daters. Other embodiments include Matches between daters and people who are not users. Daters are considered Matched when they are given the opportunity to interact with one another; for example, via chat. Matched daters may take a number of different actions after being Matched. For example, Matched daters may communicate, may decide to go out on a date, or may opt to not communicate at all. When possible, the system gathers data on the outcome of a Match.

In the preferred embodiment, a dater may request to delete a Match. When this happens, the system severs the connection between the daters in the Match. In some embodiments, this is permanent. In other embodiments, a dater, a Friend, or the system may at some point attempt to restore the Match. In the preferred embodiment, the intended application is to romantically Match two users. Other embodiments may group two or more entities together, or may group entities for reasons other than romance.

In developing this invention, a number of pitfalls have been identified and addressed regarding the interpretation of ratings. For example, a naïve implementation may judge a pairing by simply averaging all ratings on that pairing; however, such an averaging scheme may bias the result toward the dater with the most Friends contributing ratings. In preferred embodiments, ratings from each Friend Group are combined or averaged together first and considered as a unit. Another mistake is to consider ratings to be independent. In a best-case scenario, ratings are only conditionally independent given the pairing; in a worst-case scenario, they may be highly correlated. In preferred embodiments, ratings with likely correlation are combined with a regression analysis to remove correlations. Another mistake is to disregard the unique statistical information afforded to a system that implements Friend Groups. Friend Groups tend to rate many of the same profiles, which allows the system to identify particular patterns between raters in the Friend Group, and exploit these patterns in making future inferences.

In some embodiments, a simple weighted average is calculated to analyze ratings received. Each evaluator in a Friend Group has a numerical weighting that weights that evaluator's rating compared to other evaluators in the Friend Group. In one embodiment, the dater may control the weightings through an input mechanism on the client interface. In another embodiment, the weightings are determined heuristically. For example, daters may be weighted higher than Friends, which may in turn be weighted higher than matchmakers. In some embodiments, these weightings may be adjusted up or down based on perceived accurate or inaccurate rating performance, respectively.

The preferred embodiment makes use of various Scores, which is a way of describing the processing of probabilistic understanding of evidence. A Score is a representation of a belief held by the system. In the preferred embodiment, each Score is a set of statistical parameters that defines a probability distribution. The preferred embodiment involves two kinds of Scores: Unidirectional Scores and Bidirectional Scores. A Unidirectional Score represents the system's belief of how one dater will like another dater; in the preferred embodiment, the measurement is to occur after the daters meet, so the belief may be a speculation of a hypothetical meeting. A prior Unidirectional Score is one calculated by the system before any ratings are received regarding the particular pairing, but considering past ratings by and of the daters. An Individual Unidirectional Score (X→Y) is based on a rating by a member of a dater (X)'s Friend Group, of another dater (Y) outside the Friend Group. A Group Unidirectional Score is calculated by probabilistically combining all available information on and ratings of a particular dater outside of a Friend Group on behalf of a dater in that Friend Group. The Group Unidirectional Score may be initialized as the prior Unidirectional Score, as if the system had rated each dater on behalf of the other dater.

A Bidirectional Score represents the system's belief in the quality of a pairing of daters. Before ratings are received regarding a pairing, the system may calculate a prior Bidirectional Score by combining the two prior Unidirectional Scores via a heuristical combination function, or may calculate a prior Bidirectional Score directly, as if the system provided a rating as a matchmaker. A Group Bidirectional Score is calculated by combining, via a heuristical combination function, the two Group Unidirectional Scores, one from each dater's Friend Group of the other dater. An Individual Bidirectional Score is calculated based on one matchmaker's rating of a pairing. An Overall Bidirectional Score is calculated by combining all available information on and ratings related to a pairing, including all Individual Bidirectional Scores and the two Group Unidirectional Scores for the pairing.

FIG. 1 shows a flowchart of events contributing to a single Match between two daters. The process is parallelized: actions and flows may occur simultaneously. Processes may continue even if a user or agent does not respond, as may any ad lib action by the system, such as soliciting a new evaluation, or issuing a Match.

First, the system acknowledges a dater who needs a Match 100. The system searches for other daters with mutually satisfying filtering criteria 102.

Next, the system determines if the search was successful 104. If no other daters with satisfying criteria are found, and/or the dater does not satisfy the criteria of other daters, then the search is considered unsuccessful. In this case, the system schedules a future search 106. If the system finds one or more daters who satisfy the dater's filtering criteria and vice versa, and the dater satisfies the filtering criteria of one or more of the suitable daters the system identified in the search, then the search is considered successful. In this case, the system selects one of the daters from the search to be paired with the dater the system was searching on behalf of 108. The result is a pair of daters.

For each dater in the pair, the system initializes a prior Group Unidirectional Score 110. Each Score represents how the system believes one dater will like the other, prior to the system's receiving any evaluations.

The system combines these Scores into an Overall Bidirectional Score 112. The system determines if the Overall Bidirectional Score supports a Match 114. In the preferred embodiment, a Match requires that the Overall Bidirectional Score represents a high certainty of the pairing being a high quality, relative to both daters' other potential Matches.

If the system determines the Overall Bidirectional Score does not support a Match, the system then selects one or more users from the dater's Friend Group and/or matchmakers to evaluate the pairing of daters 126. Evaluations of the pairing are prioritized if the pairing has high potential for being a good pairing, but too much uncertainty to warrant an immediate Match. Next, the system solicits the selected evaluator(s). In a preferred embodiment, requests for evaluations enter a buffered Serve Queue, in which case the system adds the pairing as an entry to the Serve Queue of the selected evaluator(s) 128. At this point, the evaluator(s) are given an opportunity to evaluate the profile 130 and the system stores the evaluation(s).

To properly consider an evaluation, the system must determine what kind of evaluator it came from 132. If the evaluation came from a matchmaker, the system calculates an Individual Bidirectional Score for each evaluation, based on history 138. The system then combines this and other Scores into an updated Overall Bidirectional Score for the pairing 112. If the evaluation came from a dater or a Friend of a dater, the system calculates an Individual Unidirectional Score for each evaluation, based on history 134 (see FIG. 4). The system then updates the Group Unidirectional Score of each dater's Friend Group by combining the Individual Unidirectional Score(s) within each group 136. The system then combines the Group Unidirectional Scores and possibly other Scores into an updated Overall Bidirectional Score for the pairing 112.

If at some point, the system determines that the Overall Bidirectional Score supports a Match, the system Matches the daters and invites them to chat 118. In this embodiment, daters are considered Matched when they both receive an invitation from the system to chat with one another 118. If the daters chat, the system stores and relays messages 124. The system may also gather feedback on the quality of the outcome 122. This may take the form of questions asked of the daters and/or evaluator(s), surveys, and so on. The system may also continue to gather evaluations from one or more additional users to build history 116. The system may also notify other users, including the evaluator(s), of the Match 120.

Figure 2:
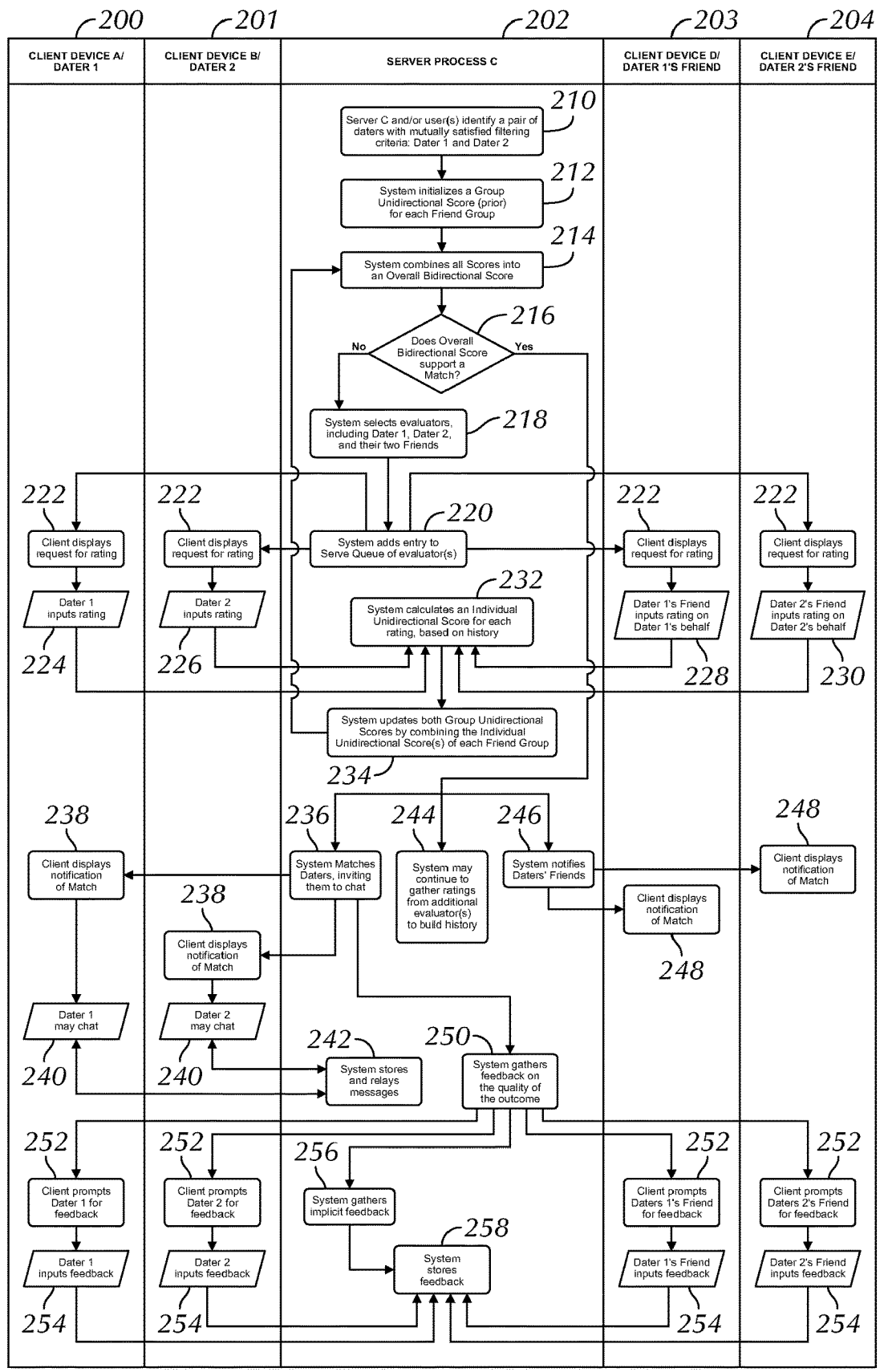
FIG. 2 illustrates the overall flow of events shown in FIG. 1, as carried out in an embodiment of the system, with events distributed between a server and multiple client devices.

As illustrated in FIG. 2, the flow of events as described in FIG. 1 may be distributed between a host computer server 202 and one or more client smartphone devices 200, 201, 203, 204 employed by users serving as daters 200, 201 and Friends of daters 203, 204. FIG. 2 shows the main processes involved in a single hypothetical pairing in an embodiment, starting from the top and following the arrows to the bottom, divided into columns by device.

The process begins 210 when Server Process C 202 and/or users identify a pair of daters with mutually satisfied filtering criteria: Dater 1 200, using Client Device A, and Dater 2 201, using Client Device B. The system initializes a (prior) Group Unidirectional Score for each Friend Group 212. Dater 1's Friend Group consists of users including Dater 1 200 and Dater 1's Friend 203. Dater 2's Friend Group consists of users including Dater 2 201 and Dater 2's Friend 204.

The system combines all Scores into an Overall Bidirectional Score 214. Next, the system determines if the Overall Bidirectional Score supports a Match 216. If the Overall Bidirectional Score does not support a Match with enough confidence, the system prepares to solicit evaluations. The system selects evaluators from each Friend Group 218, including Dater 1 200 and Dater 1's Friend 203 from Dater 1's Friend Group, as well as Dater 2 201 and Dater 2's Friend 204 from Dater 2's Friend Group.

The system adds the entry of the pairing of Dater 1 and Dater 2 to the Serve Queue of the selected evaluators 220. For each evaluator selected, the evaluator's client device 200, 201, 203, 204 syncs with Server C 202. The client device displays the request for an evaluation 222. At some point, each selected evaluator may input an evaluation 224, 226, 228, 230. Server C 202 stores any evaluations. For each evaluation, the system calculates an Individual Unidirectional Score based on the history of the evaluator 232, since the evaluator is a Friend and not a matchmaker. As necessary, the system updates the Group Unidirectional Score for each Friend Group by combining the Individual Unidirectional Scores within each Friend Group 234. As necessary, the system updates the Overall Bidirectional Score of the pairing by combining the Group Unidirectional Scores from the Friend Groups of the daters in the pairing 214.

If at some point, the system determines that the Overall Bidirectional Score of the pairing supports a Match, the system Matches the daters 236. Daters are considered Matched when they are notified of the Match by the system 238 and invited to chat 240. Should the daters choose to chat, Server C 202 stores and relays messages 242 between client devices 200, 201. The system may also notify the respective Friend Groups of the daters 246, including the Friends who evaluated the pairing. If so, the client devices of the daters' Friends display notification of the Match 248. The system may also continue to gather evaluations from additional evaluators to build history 244.

After a Match is made, the system may gather feedback on the quality of the outcome 250. This may take the form of feedback from users, including but not limited to follow-up questions about the daters in the Match, questions about whether or not a date occurred following the match, a survey about the evaluations experience, and so on. If this occurs, the system sends a request to the client devices of users selected for feedback. The client device of each selected user prompts the user for feedback 252. If the user inputs feedback 254, the system stores this feedback 258. The system may also gather implicit feedback 256 and store it 258.

Figure 3:
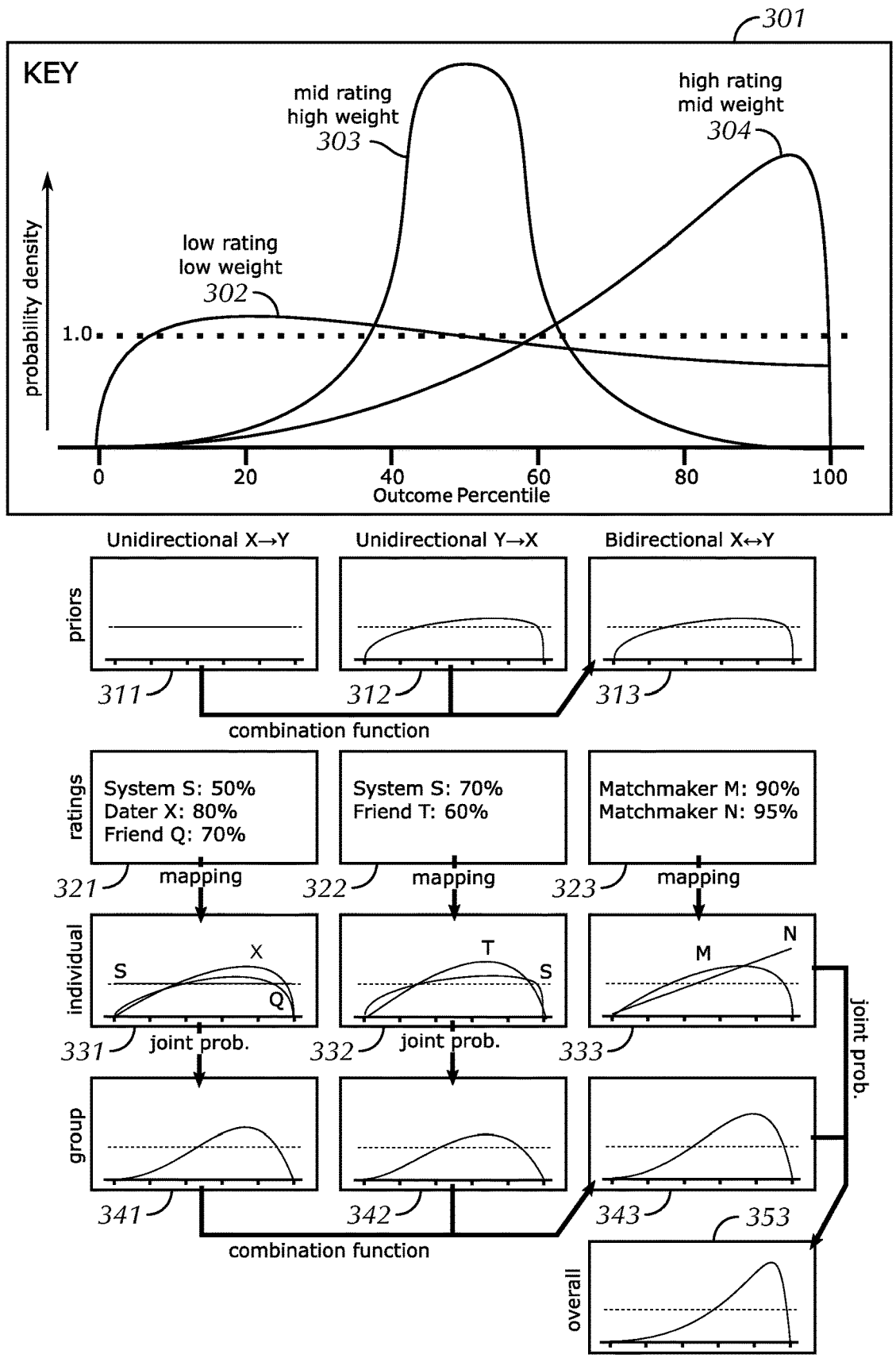
FIG. 3 illustrates a preferred embodiment of the means by which the system generates and combines the various Scores described in FIG. 1 and FIG. 2.

FIG. 3 illustrates a preferred embodiment for generating and combining the various Scores that are mentioned in FIG. 1 and FIG. 2. In the preferred embodiment, each Score is a set of numbers that parametrize a probability distribution. The details of the probability distribution depend on whether the Score is Unidirectional or Bidirectional. For a Unidirectional Score XY, the sample space represents how Dater X would rate Dater Y as a potential romantic partner after getting to know Dater Y. For a Bidirectional Score X⇆Y, the sample space represents the quality of a potential romantic pairing between Dater X and Dater Y if they were to get to know each other. Therefore, all Scores have an inherent uncertainty, because the ratings on which they are based are made in advance of the daters actually meeting. Only after the system issues a Match and the daters get to know one another can the system determine a more precise true outcome based on feedback, and even then there is some uncertainty.

Figure 4:
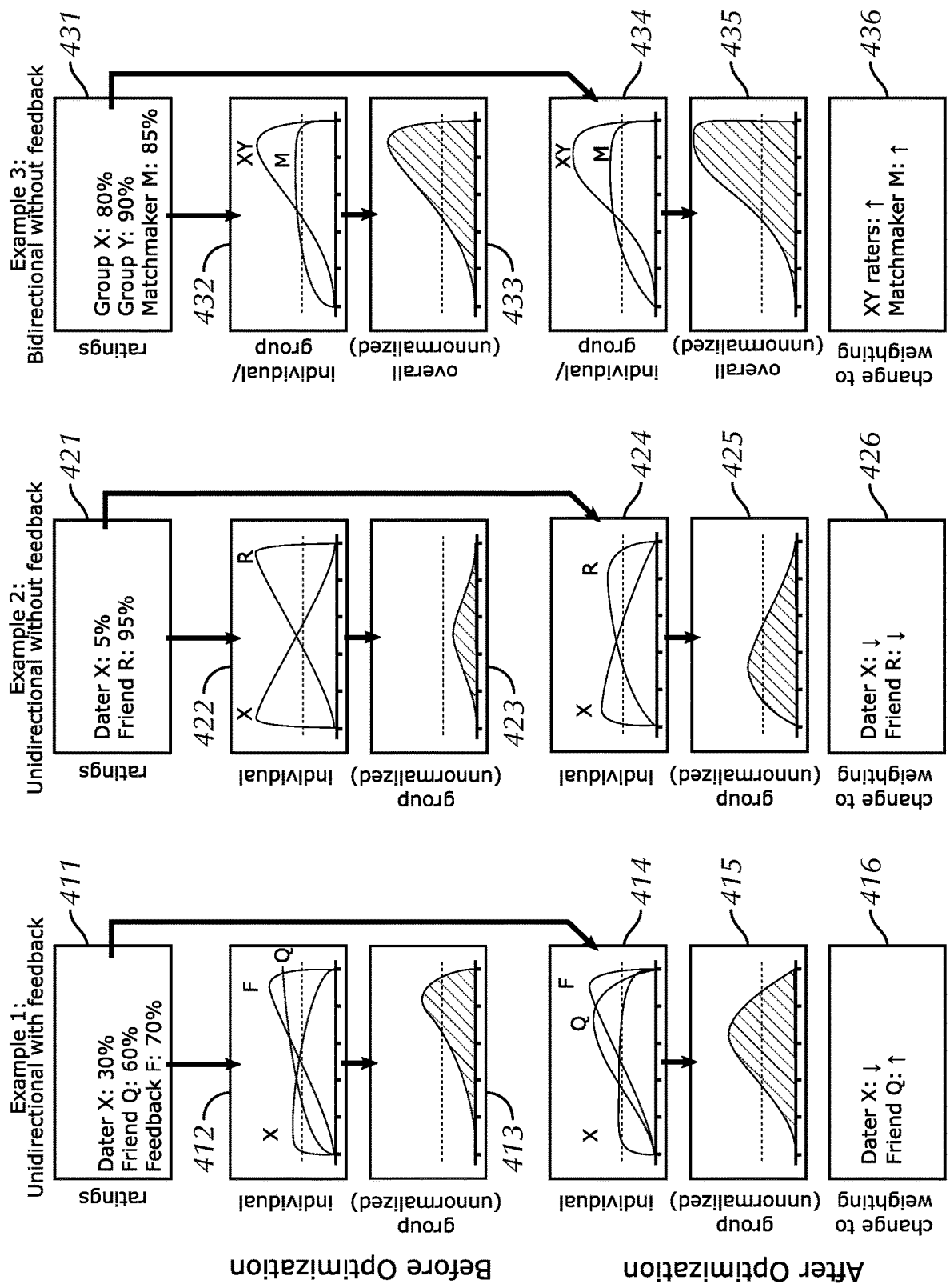
FIG. 4 illustrates how the system calculates the mapping parameters that are used to map a particular rater's rating to an Individual Score that sets the probability density function for that rating.

In a preferred embodiment, the outcomes are quantified from 0%, being the worst, to 100%, being the best. As a simplification, the outcomes are normalized on a percentile basis, so that a uniform probability distribution corresponds to the uninformative prior. So for example, a Unidirectional X⇆Y outcome of 20% means that dater X would prefer dater Y over 20% of the available options, all things considered. A Bidirectional Score X⇆Y of 90% means that Dater X and Dater Y make a better couple than 90% of possible pairings of available daters. FIG. 3 and FIG. 4 contain a number of various probability density functions (pdf). In each plot, the vertical axis is probability density, and the horizontal axis is the percentile measure of the Unidirectional or Bidirectional outcome, depending on context.

The figure key 301 shows several hypothetical probability distributions, exaggerated for illustrative purposes. Curve 302 represents a low rating, since the area under its curve is biased to the left, towards lower percentile outcomes. It also represents a low weighting (low conviction of belief), since the curve has a large spread and does not deviate much from unity. The endpoints of this curve signify that a worst-case outcome of 0% is ruled out by this Score, whereas a best-case outcome of 100% is not. Curve 303 represents a middling rating, since its area is heavy in the center, and a high weight, since is has a narrow spread and has high density at its peak. The endpoints signify that a best- and worst-case outcome are ruled out. Finally, curve 304 represents a high rating, since its area tends to the higher outcomes, and it has a middling weight since it has a medium spread. The endpoints signify that a best- and worst-case outcome are ruled out. Many of the curves shown are different parametrizations of the beta distribution, which has two shape parameters. In this case, the two parameters are related to the mean and standard deviation of the distribution, and together constitute the Score underlying the distribution. A Score may be said to be "high" or "low" if the resulting pdf is biased toward high or low outcomes, respectively. Other embodiments may have different ways to parametrize the probabilities, or even allow for multidimensional outcomes.

In the preferred embodiment, the pdfs are defined as beta distributions, which have two shape parameters, $(\alpha-1)$ and $(\beta-1)$, which can be thought of as "for" votes and "against" votes, respectively. A Score with a higher $(\alpha-1)$ than $(\beta-1)$ is a high Score, and corresponds to a high probability of a positive outcome. A Score with a high total $(\alpha-1)+(\beta-1)$ is a highly weighted Score, and corresponds to a high certainty of belief. Performing a pointwise product of multiple beta distributions is equivalent to summing the "for" votes and "against" votes of all the components. Therefore, using beta distributions is equivalent to a voting system where fractional votes for and against may be cast.

Another simple embodiment of the pdfs is the use of the gaussian distribution, which has two shape parameters, $\mu$ and $\sigma^{-2}$, which are the mean and precision (inverse variance), respectively. A high $\mu$ corresponds to a high Score, and a high $\sigma^{-2}$ corresponds to a highly weighted Score. Performing a pointwise product of multiple gaussian distributions is equivalent to performing a weighted average of the means weighted by the precisions to arrive at a combined mean, and summing the precisions to arrive at a combined precision. Therefore, using gaussian distributions is equivalent to weighted-average voting system.

FIG. 3 continues with a hypothetical pairing of two daters, Dater X and Dater Y. The first use of Scores is when the system assigns prior Unidirectional Scores 110, 212. In this example, Dater X is a relatively new user and the system does not have any information yet about the type of partner that Dater X is looking for. The system does not have any information on which to base an initial rating, and therefore uses the uniform prior distribution 311, $(\alpha-1)=0.0$ and $(\beta-1)=0.0$. The system does have some evidence that Dater Y will like Dater X, and so initializes a prior corresponding to a 70% rating, but with a low weight, as the evidence is only circumstantial. This curve corresponds to a beta distribution with $(\alpha-1)=0.4$ and $(\beta-1)=0.1$.

Next, the system combines the two prior Unidirectional Scores 311, 312 into a Bidirectional prior 313. This process is mentioned in the previous figures 112, 214. This process employs a combination function that takes in two Unidirectional Scores and estimates the resulting Bidirectional Score of the pairing. The combination function may depend on other factors affecting the potential pairing. In a preferred embodiment, the combination function is a heuristic, possibly based on user history of Match outcomes. In general, if either or both Unidirectional Scores are low, the resulting Bidirectional Score will be low also, indicating a poor pairing, since a good pairing requires mutual liking. A high Bidirectional Score, roughly speaking, results from two Unidirectional Scores that are relatively high and similar, indicating a balanced match. In this example, since the X→Y prior is uniform, the X⇆Y prior is just inferred to be the same as the Y→X prior, but a more complex combination function may yield different results.

The next occasion for the system to use Scores is in the process of selecting raters to solicit (not shown). To facilitate this task, the system may keep a prioritized list of potential pairings for each dater. In a preferred embodiment, the prioritization is determined by a function of the Bidirectional Score, including uncertainty and expected outcome. An example of a high priority pairing is one with a high score, but not quite enough certainty to warrant a Match—the system will try to get an additional rating as soon as possible to hopefully verify that the pairing is quality and deserves a Match. An example of a low priority pairing is one with a low expected outcome combined with high certainty—in that case, the pairing is unlikely to ever result in a Match, and so it does not behoove the system to waste the time of a rater. Furthermore, the system may solicit raters based on their having a high weighting in regards to the pairing (variable weighting will be discussed in FIG. 4). Or, the system may in some cases solicit additional raters for highly-certain scores in order to calibrate the weighting of unestablished raters.

The hypothetical example picks up after five ratings have been received 321, 322, 323 in addition to the system-derived priors. Dater X has rated Dater Y 80%, and, Dater X's Friend Q has rated Dater Y 70% on behalf of Dater X 321. Meanwhile, Dater Y was unavailable to rate, so Dater Y's Friend T was chosen by the system as an accurate proxy for Dater Y, and Friend T rated Dater X 60% on behalf of Dater Y 322. Lastly, the system employed the help of two third-party matchmakers, Matchmaker M and Matchmaker N, who rated the pairing of X with Y 90% and 95%, respectively. Based on the prior accuracy of each rater, the system maps each person's rating to a Score, each of which parametrizes a pdf. This mapping is performed using a function, along with personalized mapping parameters, which are discussed in FIG. 4. In the preferred embodiment, the mapping function is monotonically increasing so that a higher rating always maps to a higher Score (a higher rating implies better outcomes are more probable). The ratings from the daters and their Friends map to Individual Unidirectional Scores 331, 332, and the matchmakers ratings map to Individual Bidirectional Scores 333. For reference, these mappings correspond to items 134, 232, and 138 in the previous figures. For the X→Y Scores in this example, Dater X has a middling weight, $(\alpha-1)=1.0$ and $(\beta-1)=0.2$, 331X, Friend Q has a low weight, $(\alpha-1)=0.6$ and $(\beta-1)=0.2$, 331Q, and the system has zero weight, $(\alpha-1)=0.0$ and $(\beta-1)=0.0$, 331S. For the Y→X Scores, the system has a low weight, ($\alpha-1$)=0.4 and ($\beta-1$)=0.1, 332S and Friend T has a high weight, ($\alpha-1$)=1.2 and ($\beta-1$)=0.6, 332T. Finally, for the Individual X⇆Y Scores, Matchmaker M and Matchmaker N both have middling weights, ($\alpha-1$)=0.8 and ($\beta-1$)=0.2, and, ($\alpha-1$)=1.0 and ($\beta-1$)=0.0, respectively 333.

Next, the system combines the Individual Unidirectional Scores from each dater and that dater's Friends, resulting in two Group Unidirectional Scores 341, 342. In the preferred embodiment, the combination is performed as a joint probability of all the pdfs; if the ratings are believed to be conditionally independent, then the joint probability is simply a normalized pointwise product of all the individual pdfs. In this simple example, no correlations are considered, and the resulting scores are just the sums of the ($\alpha-1$) and ($\beta-1$) parameters. This results in a the two Group Unidirectional Scores being ($\alpha-1$)=1.6 and ($\beta-1$)=0.4 331, and ($\alpha-1$)=1.6 and ($\beta-1$)=0.7 342. Therefore, it is helpful to use similar functional forms for all the pdfs, such as gaussian or beta distributions, which can be combined pointwise by simple algebraic combinations of the individual parameters. If the system believes that the ratings are not conditionally independent, it must account for the correlations by adjusting the weighting of the resulting Group Unidirectional Score. Such situations are bound to occur frequently, since Friends are often "on the same wavelength." This effect is more pronounced in cases where users, before making their own rating, are made aware of previous rating(s) made by Friend(s). In some embodiments, the system may explicitly share this information. But also, the system should be on guard for the possibility of Friends colluding to "stack" ratings to the benefit of a dater. In any case, the likely result is for ratings to be positively correlated, in which case the system should decrease the weighting of the Group Unidirectional Score accordingly, by application of a regression analysis.

Next, the system combines the two Group Unidirectional Scores into a Group Bidirectional Score 343, which measures the quality of the pairing based on the combined ratings from the two Friend Groups, possibly including from one or both daters. For reference, the process of combining the pdfs from 331 and 332 into 343 corresponds to process 112 and process 234 in the previous figures. In the preferred embodiment, this step uses the same heuristic combination function mentioned previously. In this example, since both Group Unidirectional scores are relatively high in the 60-80% range, the resulting Bidirectional Score is also relatively high, with good confidence (high weight). In this example, the combination function is simply a pointwise product of the two pdfs, so the resulting Group Bidirectional Score is ($\alpha-1$)=3.2 and ($\beta-1$)=1.1 343.

Finally, the system combines the Individual Bidirectional Scores 333 from the matchmakers with the Group Bidirectional Score 343 to produce an Overall Bidirectional Score 353. In this instance, since the matchmakers are likely unacquainted with the Friends or the other matchmakers, their ratings are likely conditionally independent. Therefore, they may be combined by computing the joint probability directly. In this example, the resulting Overall Bidirectional Score is high with medium-high certainty: ($\alpha-1$)=5.0 and ($\beta-1$)=1.3.

Having computed the Overall Bidirectional Score, the system determines whether a Match should be made. In the preferred embodiment, the system issues a Match whenever the Overall Bidirectional Score pdf reaches predetermined thresholds indicating a high likelihood of a successful pairing. Some embodiments may have additional considerations, such as ensuring that every user receives a reasonable number of Matches; however, in the preferred embodiment, proportioning out Matches evenly is aided by employing a well-chosen combination function and thresholds for Matching.

If the system determines that a Match is not currently warranted, it may continue to gather ratings from members of the Friend Groups or from matchmakers. When a new rating is received, the system simply adds the rating to the appropriate list—321, 322, or 323, for example—and propagates the changes through the process in order to update the Overall Bidirectional Score.

FIG. 4 illustrates how the system calculates the mapping parameters that are used to map a particular rater's rating to an Individual Score that sets the pdf for that rating (i.e., the mapping between 321 and 331). Recall that the Individual Score encapsulates properties including the expected value of the outcome and the certainty of the outcome (weight of the rating). Therefore, given a rating of say 60%, the system must determine how to assign a mean outcome and weight, and possibly other shape parameters. In the preferred embodiment, this mapping function is a heuristic function with several personalizable parameters. Initially, before a rater has established a history of ratings, the system uses a default set of parameters to perform the mapping. These default parameters are a prior, based on an analysis of historical ratings and outcomes system-wide. After a rater has started to establish a rating history, the mapping parameters become increasingly personalized, by applying a Bayesian approach.

Essentially, the system adjusts the mapping parameters of each rater to find the most probable collective set of parameters system-wide (or over a subset of raters), given the results of all the outcomes known system-wide (or from a representative training set). Mapped pdfs are more probable when they are in agreement with each other and with the recorded outcome, if available. This agreement may be computed in a number ways, including the concordance correlation coefficient; or, in a preferred embodiment, the system simply performs a slightly modified version of the joint probability combination, e.g. 321→331. Specifically, it uses the normalization constant used to compute the Group Score pdf, i.e., the area under the Group Score pdf after performing the joint probability, but before normalization. If the area is small (for example, 423), it means that the pdf for one or more raters was strongly inconsistent with each other or a pdf corresponding to feedback on a Match. The system adjusts the mapping parameters to create more consistency between the pdfs.

Example 1 in FIG. 3 illustrates a more in-depth scenario in which feedback is available. This situation concerns the pairing of Dater X with Dater Z (not shown). The system recorded a rating of 30% from Dater X, and 60% from Dater X's Friend, Friend Q 411. The system ended up issuing a Match for the pairing. Despite giving a low rating initially, Dater X was pleasantly surprised by Dater Z in person, and responded with positive feedback, which the system interprets as being in the 70th percentile, with some uncertainty. Using the pre-optimized mapping parameters, each rating is mapped to a pdf, and the feedback is also mapped to a pdf 412. When these three pdfs are combined using the joint probability procedure, accounting for correlation as previously noted, it results in a certain unnormalized pdf 413. This pdf has relatively small area, indicating that the constituent pdfs are somewhat inconsistent. In this case, the inconsistency results from Dater X being weighted too strongly in the calculation.

After the optimization process, based on this pairing and possibly others not shown, the system determines that Dater X should be weighted less strongly, and a low rating not interpreted as emphatically; meanwhile, Friend Q should be weighted stronger 414. The system tunes the mapping parameters to increase the concordance 415, while also choosing mapping parameters that are likely, given the system-wide distribution of mapping parameters, and also consistent with a monotonically increasing mapping function. Both these considerations help to prevent over-fitting. To summarize, Dater X's weighting decreases and Friend Q's weighting increases 416, henceforth.

Example 2 shows how the process can be used to analyze ratings where a pairing does not result in a Match, or feedback is not available. Even without feedback, pdfs can still be compared to one another to maximize self-consistency. In this example, Dater X has rated a certain profile 5%, while Friend R has rated the same profile 95% on behalf of Dater X 421. Based on the pre-optimized weighting parameters, the system maps Dater X's rating to a markedly low pdf 422X, while the system maps Friend R's rating to a markedly high pdf 422R. The resulting group score indicates that the truth is somewhere in between, but the small area 423 is indicative of the incongruity of the system believing both ratings strongly.

After a round of optimizing system parameters, the system computes the new pdfs 424. The joint probability of these is now more internally consistent, since the unnormalized group pdf has a larger area 425. In this case, the weighting for each rater decreases (in regards to rating for Dater X) 426. The weighting for Friend R may decrease more, if for example, system-wide history shows that daters are better than their Friends at predicting outcomes, or for example, if Dater X specifically has an accurate history of rating.

Example 3 shows how the same analysis can be performed for Bidirectional Scores. The process works the same, only the outcome refers to the success of the pairing, rather than the feelings of one dater towards another. In this example, a group of Friends representing a Dater X has given Dater Y a composite rating of 80%, while a group of Friends representing Dater Y has given Dater X a composite rating of 90%, and a third-party matchmaker has rated the pairing 85% 431. Before optimization, the combination function is used to combine the two Unidirectional Scores into a Bidirectional Score 432XY. Similarly, based on the pre-optimized personalized mapping parameters for Matchmaker M, the system computes a Bidirectional Score 432M. When these two Bidirectional pdfs are combined, the resulting Overall pdf has a relatively large area 433, due to the agreement of the two Bidirectional pdfs.

To increase the concordance, the system increases the weighting of the individuals that contributed to the high Group XY Score, producing a higher weighted Group XY pdf 434XY. The system also increases the weighting for Matchmaker M, and also adjusts Matchmaker M's mapping parameters to map the rating to a higher mean 434M. The resulting concordance is larger than before 435, since both pdf M and pdf XY become more concentrated in the same outcome range. In summary, all the raters involved are bumped up in weighting due to their agreement 436, even though no feedback was available at the time.

Figure 5:
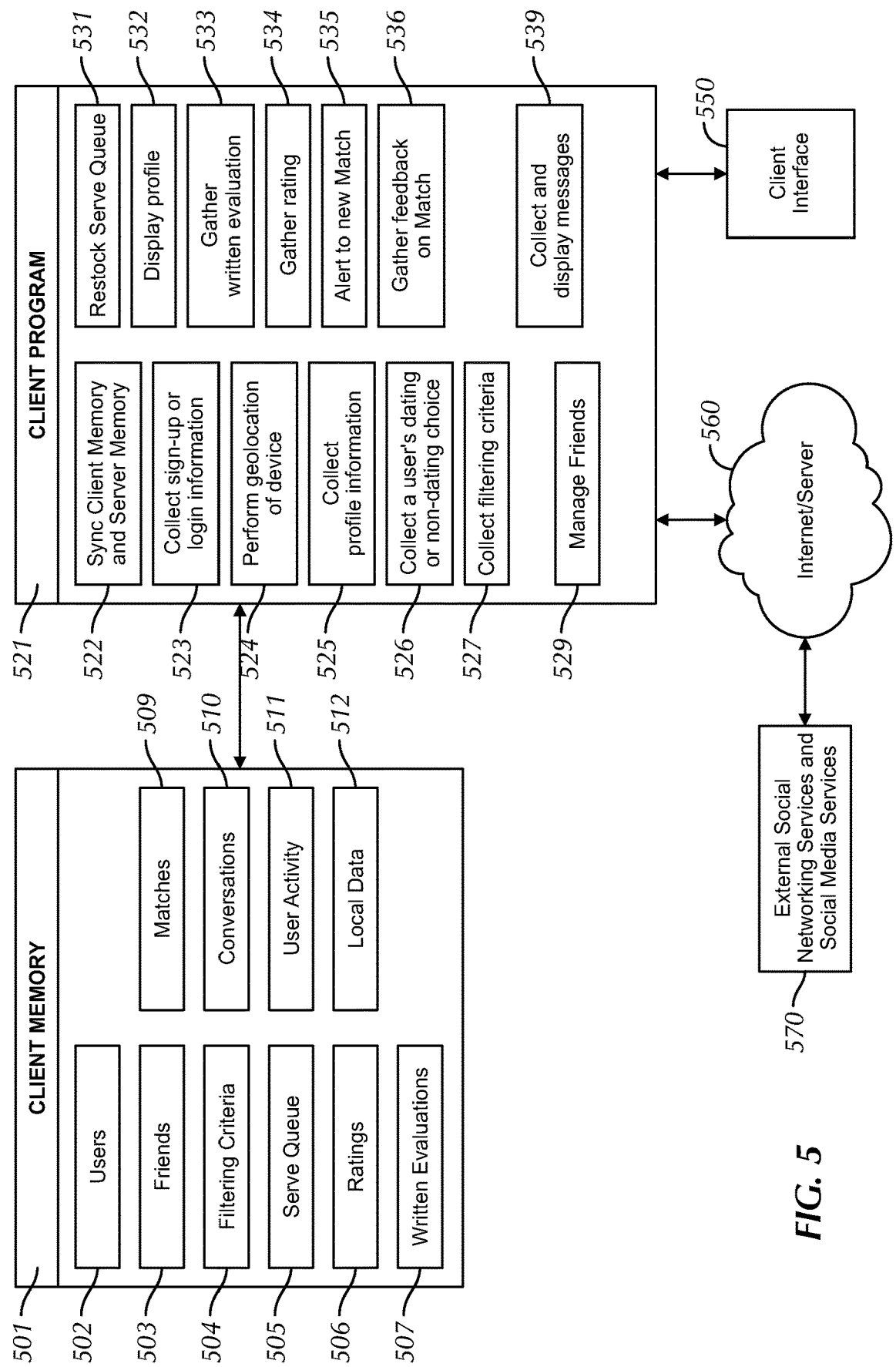
FIG. 5 illustrates the layout of the Client side of an embodiment of the dating system distributed between a Server side and a Client side.
Figure 6:
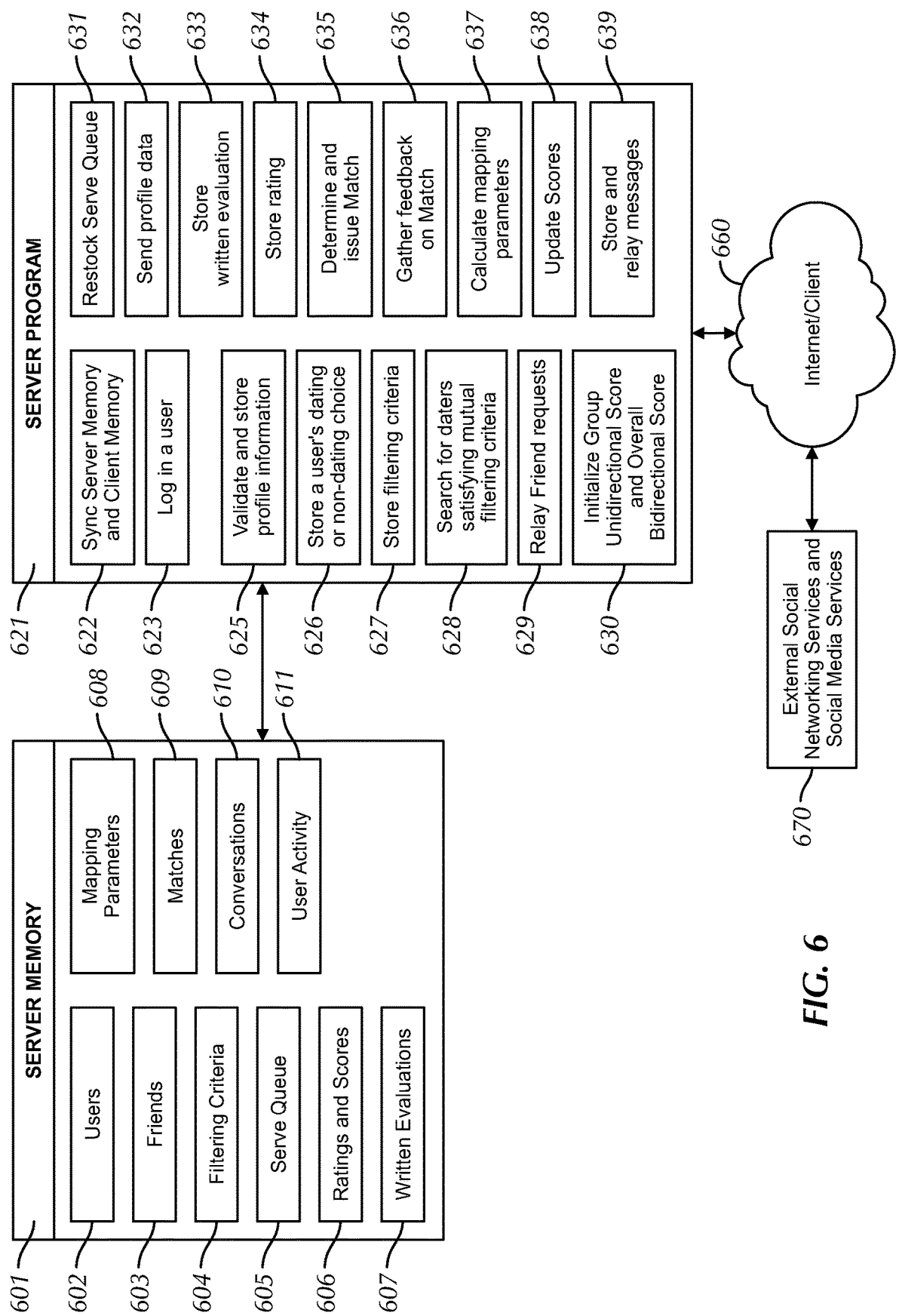
FIG. 6 illustrates the layout of the Server side of an embodiment of the dating system distributed between a Server side and a Client side.

FIG. 5 and FIG. 6 illustrate the preferred distribution of processing between a Server side and a Client side, although different embodiments may distribute the functions and memory storage differently. The Server side is made up of a Server Memory 601 and Server Program 621, while the Client side is made up of a Client Memory 501, Client Program 521, and Client Interface 550. The system comprises at least one instance of the Server Memory and Server Program. Each end-user is associated with at least one instance of the Client Memory, Client Program, and Client Interface; for example, the client components may be be a web page running on a user's device, a mobile application running on a user's smartphone, or a standalone application running on a user's computer. For simplicity, the following descriptions assume one instance of a Client Program for each user and one instance of the Server Program running on a centralized Server.

In some embodiments, these functionalities may be fragmented over multiple instances running on multiple computer devices running in parallel, or be run on as few as one computer. For convenience, the following describes an embodiment in which the Server Memory and Client Memory are divided up into specialized named databases (to be described in the following sections) stored in a non-relational database such as MongoDB. Most of the named databases in the Server Memory have corresponding named databases in the Client Memory. Unless otherwise stated, the Client Memory is a subset of the Server Memory, of entries that are pertinent to that particular user. These databases are intended to be synced continually by the Client Program and Server Program running in the background, as detailed below. Other embodiments may organize the information differently, but the intent is the same.

The preferred embodiment utilizes the Distributed Data Protocol, a system for handling database synchronization and communication, across a WebSocket duplex transport, with a SockJS WebSocket emulator as fallback. Each Client Program may issue "subscribe" directives to the Server Program for database queries needed to display the Client Interface. In turn, if the Server Program determines that the user has access to the requested entries, it "publishes" the entries to the proper Client Program. Unless otherwise noted, the Server Program keeps a record of the subscriptions in memory; when changes are made to the Server Memory that affect the subscription query, the Server Program sends the affected Client a list of "added", "changed" and "removed" commands that instruct the Client Program to add entries, change entries, or remove entries from the Client Memory, respectively.

Once the Client Program determines that it no longer needs a subscription to certain data, it may send a message to the Server Program to stop the subscription. For example, after an evaluator submits an evaluation of a profile, the Client Program stops the subscription for any data pertaining to that profile; the Client Program may re-subscribe to the data if it is needed later in a different context, such as if the dater follows an embedded link to the profile from a chat message. The Server Program also stops subscriptions when the user logs off or the WebSocket closes due to inactivity. The Server Program may publish data not explicitly requested by the Client Program if it anticipates the Client needing the data. For example, when the Server Program adds a Serve Queue entry (solicits an evaluation), it may automatically subscribe the Client Program to any data needed to display the profile.

The Client side is made up of a Client Memory 501, a Client Program 521, and an internet connection 560 to the Server Program 621 on the Server side. The Client side also contains a Client Interface 550 which allows the user to visually interact with the Client Program 521 and communicate information to the system.

Each Client device has its own store of data, the Client Memory 501. In the preferred embodiment, it is implemented as a RAM-based database emulator, but may comprise any store of data on a client device.

The Client Memory 501 may contain a Client Memory Users database 502 containing a subset of the Server Memory Users database 602, as well as changes to a user's own entry yet to be uploaded to the server. The subset contains the profile for a user, and the public part of other users' profiles as necessary—such as Friends, Matches, or daters in a user's Serve Queue—whose names and headshots may be displayed at times. Pseudo-public information may be obfuscated to ensure privacy, for example: age instead of birthdate, and distance instead of location. An example of a user's own entry in JSON might read:

```
{
    UserId: "RasEPSwH82DQlNZdf",
    externalServices: {friendbook: {
            accessToken: "JEi38NFj392hFueks8sdFJ8JKj30fjaQoi",
            expiresAt: 1479589283741,
            id: "12345671234567"}, }
    isDater: true,
    publicProfile: {name: "John", age: 28, gender: "male", photos:
        ["/images/1239847392129387.jpeg"], bio: "I applied to be an
        astronaut!" },
    privateProfile: {DOB: "1989-02-22", geolocation: [-77.1243143,
    38.4231435],
        lastOnline: 1490931509}
}
```

The Client Memory 501 may contain a Client Memory Friends database 503 containing a subset of the Server Memory Friends database 603, as well as changes to Friend status yet to be uploaded to the server. The subset is restricted to users who are the user's Friends. An example JSON entry may be: {UserId: "RasEPSwH82DQ1NZdf", FriendUserId: "P2fNb3T2Aq982Nve", status: "confirmed"}

The Client Memory 501 may also contain a Client Memory Filtering Criteria database 504 containing a subset of the Server Memory Filtering Criteria database 604, as well as changes to the user's own entry yet to be uploaded to the server. In the preferred embodiment, the Client Memory 501 only contains up to one entry, the entry that corresponds to that user's personal filtering criteria, if that user is registered as a dater. In other embodiments, a Friend of a dater may be able to specify narrower filtering criteria than the dater's own criteria, in which case the Client Memory of the Friend contains the pertinent entries as well. An example entry in JSON may be: {UserId: "RasEPSwH82DQ1NZdf", myAge: 28, preferredMinAge: 23, preferredMaxAge: 33, myGender: "male", preferredGenders: ["female"], searchRadius: 0.00505, position: {type: "Point", coordinates: [-77.1243143, 38.4231435]}}

The Client Memory 501 may also contain a Client Memory Serve Queue database 505, a feature used in some embodiments to ensure that evaluators receive a steady stream of profiles to evaluate. The Client database contains a subset of the Server Memory Serve Queue database 605 of queues that have the user listed as the rater. An example entry in JSON may be: {evaluatorUserId: "RasEPSwH82DQ1NZdf", onBehalfOf: "P2fNb3T2Aq982Nve", profileId: "N13Mu72VhKj3Fn390Zxw"}, or for a matchmaker evaluation: {evaluatorUserId: "RasEPSwH82DQ1NZdf", profilIds: ["N13Mu72VhKj3Fn390Zxw", "H92L3j212NbvL37L2n2s"]}

The Client Memory 501 may also contain a Client Memory Ratings database 506 containing a subset of the Server Memory Ratings database 606, as well as new ratings yet to be uploaded to the server. Entries stored on a user's device include: ratings recently made by the user but not yet uploaded to the server, and ratings to be displayed to the user, such as previous ratings by Friends associated with profiles that the user is privileged to view. An example entry in JSON may be: {evaluatorUserId: "RasEPSwH82DQ1NZdf", onBehalfOf: "P2fNb3T2Aq982Nve", profileId: "N13Mu72VhKj3Fn390Zxw", rating: 90}

The Client Memory 501 may also contain a Client Memory Written Evaluations database 507 containing a subset of the Server Memory Written Evaluations database 607, as well as new written evaluations made by the user yet to be uploaded to the server. Entries stored on a user's device include: written evaluations recently made by the user but not yet uploaded to the server, and written evaluations to be displayed to the user, such as previous written evaluations by Friends associated with profiles that the user is privileged to view. This database is only present in embodiments with a written evaluation feature. An example entry in JSON may be: {evaluatorUserId: "RasEPSwH82DQ1NZdf", onBehalfOf: "P2fNb3T2Aq982Nve", profileId: "N13Mu72VhKj3Fn390Zxw", evaluation: "She's just your type!"}

The Client Memory 501 may also contain a Client Memory Matches database 509 containing a subset of the Server Memory Matches database 609, as well as local updates to a Match status (such as un-Matching) yet to be uploaded to the server. An example entry in JSON may be: {UserId: "P2fNb3T2Aq982Nve", matchUserId: "N13Mu72VhKj3Fn390Zxw", hasBeenViewed: true, feedback: {type: "daterReportedPostMeetup", rating: 95}}

The Client Memory 501 may also contain a Client Memory Conversations database 510 containing a subset of the Server Memory Conversations database 610, as well as newly drafted or entered messages yet to be uploaded to the Server. The subset corresponds to conversations in which the user is a participant. An example entry in JSON may be: 55 ConversationId: "M39afkKk393jNZfOe", UserId: "P2fNb3T2Aq982Nve", partners: ["RasEPSwH82DQ1NZdf"], lastActivity: 1480306987126, type: "friends", messages: [
  {UserId: "P2fNb3T2Aq982Nve", content: "<a href="/profile/392jFlkj3af3Dds"><img src="/images/8Nh32Ln392Q"> </a> Why did you like her for me?", time: 1480306987126, read: false}
], draft: "I lik"}

The Client Memory 501 may also contain a Client Memory User Activity database 511 containing records of recent activity by the user yet to be uploaded to the Server Memory User Activity database 611. An example entry in JSON may be: {UserId: "P2fNb3T2Aq982Nve", lastActivity: 1480306987126}

The Client Memory 501 may also store Local Data 512 including any data needed to keep the user experience consistent between devices, such as language settings, last dater selected, etc. Although primarily intended to be stored on the user device, this data may be duplicated in the Server Memory 601 to facilitate the user's switching between multiple devices. An example entry in JSON may be: {UserId: "P2fNb3T2Aq982Nve", language: "en-US", units: "miles", lastScreen: "edit profile"}

The Client Program 521 has many functions, the main ones described below. First, in communication with the Server Program, the Client Program syncs 522 the Client Memory to the Server Memory. In the preferred embodiment, the client and server perform this joint task using the DDP protocol. When a user logs on, the Client Program 521 "subscribes" to all data it needs to operate. The Server Program 621 in turn "publishes" all the requested data, if it deems the user should have access to that data. Whenever the Client Program 521 makes a change to the Client Memory 501 that should be reflected in the Server Memory 601, the Client Program 521 sends a DDP message via the internet to the Server. Meanwhile, the Client Program 521 also receives instructions from the Server Program 621, which the Client Program 521 responds to by making the requested changes to the Client Memory 501.

Another function of the Client Program 521 is to collect signup information or collect login information 523. After running the Client Program 521 on a device, the user must register an account or login. The Client Program 521 prompts the user for identifying information and validates the user. For example, the Client Program 521 may utilize an external social network site 570 to verify that the user's information is authentic. In such case, the user is prompted to enter their login information into the social network portal. The Client Program 521 collects the social network ID, and a verification token. The Client Program 521 stores this information locally in a new entry in the Client Memory Users database 502 in the Client Memory 501 and also transmits the information through the internet 560 to the Server Program 621. This information is then sent to the Server Program 621 to be stored or validated.

Another function of the Client Program 521 is to perform a geolocation of the user's device 524, for example, by interfacing with the device's built-in GPS functionality. In the preferred embodiment, geolocation is only performed on the devices of daters, and a user may opt out of the functionality and instead provide their own location information. This information may be stored in the User Activity database 511 or the Users database 502, to be sent to the Server Program for use in finding nearby available daters.

Another function of the Client Program 521 is to collect profile information 525 from a user to be stored in the user's entry of the Client Memory Users database 502 and sent to the Server Program 621 via the internet 560 for validation and storage 625. In the preferred embodiment, the system may contain a profile of each user. Portions of the profile may be public to some or all users; other portions may be for internal use only. The user may access an edit-profile page via a menu option in the Client Interface 550 to edit their profile information. In some embodiments, Friends may also be able to add information to their Friends' profiles. The Client Program 521 may also initiate this function for a new user immediately after registering the user for the first time. On the edit-profile page, the user may supply autobiographical information, and may choose to add photos to his/her profile. In the case of photos, the Client Program 521 downloads photos of the user from an external social network 570, displays them to the user in a grid, prompts the user to select one, and finally prompts the user to zoom and crop the selected photo. The resulting image is placed in the Client Memory Users database 502. The photo link and cropping parameters are uploaded via the internet 560 to the Server Program 621. Any changes to the profile are stored in the Client Memory Users database 502 and synced to the server.

Another function of the Client Program 521 is to collect a user's preference of their dating or not-dating choice 526 from a user to be stored in the user's entry of the Client Memory Users database 502 and sent to the Server Program 621 via the internet 560 for validation and storage 626. If a user opts to be a dater, that instructs the system to find potential matches for the dater, and to make the user searchable. If a user opts to be a non-dater, that instructs the system that the user will only be a rater, and to not show the user's profile as a potential match to daters.

Another function of the Client Program 521 is to collect, or allow a user to edit, the user's filtering criteria 527. In a preferred embodiment, a dater may specify hard criteria that must be satisfied by any potential match. Such criteria may include age range, distance, and gender. These criteria are stored in the the Client Memory Filtering Criteria database 504 and uploaded to the Server Program 621 via the internet 560. In some embodiments, some search criteria may be soft: the system tries to satisfy the criteria, but they are not essential. In some embodiments, Friends of a dater may specify narrower criteria from the dater's own criteria, in which case the narrower criteria apply only to profiles being shown to the Friend for rating on the dater's behalf.

Another function of the Client Program 521 is to allow a user to manage Friends 529. In the preferred embodiment, the Client Interface 550 contains a button or menu option that takes the user to a Friends Management screen. The Client Program 521 displays the users who are currently confirmed Friends with the user, by displaying information within the Friends database 503, collated with profile information from the Users 502 database. Displayed next to every Friend is a button that allows the user to cancel that Friend relationship. The screen also shows users with a known relationship to the user but who are not Friends, and allows users to request Friendship with another user, or confirm such a request. Any changes made to a Friend status (confirmed, requested, pending, none) are noted in the Client Memory Friends database 503 and transmitted to the Server Program 621.

Another function of the Client Program 521 is to restock the Serve Queue database 531 whenever there are insufficient profiles buffered for any dater for which a user will perform ratings. This process involves receiving the profile data, including photos, and storing them in the Users database 502 when they are sent by the Server Program 621, and storing references to the profiles in the Client Memory Serve Queue database 505. The Client Program 521 may remove an entry in the Serve Queue 505 after the user completes an evaluation.

Another function of the Client Program 521 is to display a profile 532, which is necessary in several different instances. First, when a user elects to rate profiles on behalf of a Friend or for him/herself, the Client Program 521 displays one or more profiles at a time for the user to rate. Second, the Client Program 521 may display the profile of a user who is in the process of being considered for a Match to the user or a Friend of the user. Third, a Matched user may be allowed to view the profile of the other dater. Fourth, in some embodiments, a user may be able to view the profile of a Friend. In each of these instances, the profile may be displayed along with tools to interact with the profile, such as a rating bar to rate a profile, or a chat button to converse with a Match. In all cases, though, the profile contains formatted information about a user, possibly context-specific, including the user's name, photos of the user, biographical or autobiographical information, distance to the relevant dater, etc. This data is read from the Client Memory Users database 502 and formatted appropriately. If the data is unavailable, or requires refreshing (such as with the distance information), the Client Program 521 may request the data immediately from the Server Program 621.

In embodiments with written evaluations, another function of the Client Program 521 is to collect a written evaluation 533 from a user on a displayed profile 532. In some embodiments, this database may contain audio or video evaluations. The Client Program 521 stores the evaluation information, along with metadata including the user's User Id and the User Id of the dater for whom the evaluation was intended, in the Client Memory Written Evaluations database 507 and sends the data to the Server Program 621.

In embodiments with numeric ratings, another function of the Client Program 521 is to collect a rating 534 from a user on a displayed profile 532. The Client Program 521 stores this information, along with metadata including the user's User Id and the User Id of the dater for whom the evaluation was intended, in the Client Memory Ratings database 507 and sends the data to the Server Program 621. In the preferred embodiment, a rating also signifies that the user is done with looking at the profile. In that case, the Client Program 521 displays another profile from the Serve Queue 505, and removes the link to the rated profile from the Serve Queue 505.

Another function of the Client Program 521 is to receive notice of a Match and alert the user 535. When the Server generates a new Match, the Client Program finds out because a new entry is added to the Client Memory Matches database 509. The Client Program may alert the user of a new Match with a tone, vibration, or visual cue on the Client Interface 550. In the preferred embodiment, the Client Interface 550 contains a page that lists a synopsis button for each Match. When a button is clicked, the Client Program 521 displays the profile of the Match, along with any written evaluations or ratings from Friends, and a button to allow the user to initiate a conversation with the Match. In the preferred embodiment, all the data necessary for displaying a Match is collated by the Server Program 621 from the appropriate databases and sent together as a single profile, which the Client Program 521 may store for future use in the Client Memory Users database 502. In some embodiments, a Friend of a dater also receives notice when a Match is issued for the dater, if the dater opts for such information to be shared with Friends.

Another function of the Client Program 521 is to collect feedback on the outcome of a Match 536. In the preferred embodiment, the feedback is a combination of explicit and implicit information. Explicit information takes the form of feedback surveys to the Matched dater or the dater's Friend(s). For example, a survey may ask the dater how the dater felt about the Match after meeting in person, which constitutes a measure of the Unidirectional outcome. Or, a survey may ask the dater or a Friend how the relationship progressed, which constitutes a measure of the Bidirectional outcome. Implicit feedback includes information about whether the dater viewed the Match's profile, whether the dater initiated or responded to conversation, and whether substantive conversation ensued. Data on the feedback is stored in the Matches database 509 in the entry for the pertinent Match, and transmitted to the Server Program 621 via the internet 560 for use in adjusting the weighting or mapping parameters.

In embodiments with a chat feature, another function of the Client Program 521 is to collect and display messages 539 sent to or written by a user. Messages authored by a user are stored in the Client Memory Conversations database 510, along with metadata including the User Id of the author, the User Id(s) of the intended recipient(s), and a timestamp. Written messages are sent to the Server Program 621 via the internet 560. The Client Program 521 on a user's device receives messages intended for that user via updates to the Client Memory Conversations database 510, and formats and displays the sent and received messages on the Client Interface 550, on a dedicated chat page. In the preferred embodiment, users may attach links to profiles within a message; the link is displayed as a button with a headshot corresponding to the profile. When clicked, the Client Program displays the profile of the linked user 532. In the preferred embodiment, this feature is implemented by formatting messages as HTML, and inserting <a> and <img> tags appropriately.

The client side may also optionally be connected via the internet 560 to one or more external Social Graphs or Social Databases 570 (such as one belonging to an existing social networking site), or to External sites with Product Services, Directories, etc.

The primary function of the Client Interface 550 is to serve as an intermediary between the user and the Client Program 521. In embodiments that involve a desktop or mobile device with a screen, features of the Client Interface 550 may appear together on the same screen, as part of separate screens, or a combination thereof. For example, on a smartphone device, the Client Interface 550 may be broken up into a series of screens, each focused on a specific task or aspect of the Client Interface 550. For more specific aspects of the Client Interface 550 of the preferred embodiment, see FIGS. 7-10.

FIG. 6 shows an example layout of the Server side of the preferred embodiment.

The Server side is made up of a Server Memory 601, a Server Program 621, and an internet connection or other connection 660 to one or more client instances. The server side may also optionally be connected via the internet 660 to one or more external Social Graphs or Social Databases 670 (such as one belonging to an existing social networking site), or to external sites with product services, directories, etc. In a preferred embodiment, the database is structured into a number of named subset databases, as shown in the figure. For clarity, the key functionalities are listed, too.

The Server Memory 601 may include a Users database 602, which includes private information about each user, and a public profile for any user that opts to have one. The private information may include the user's name, an identifying User Id, password or password hash, birthdate, geolocation, and identifying information for external social networks such as a user id or access token. The public profile section may be editable by the user (and in some embodiments, Friends of the user), and may include photos, biographical or autobiographical information, and endorsements from Friends. The entry for a user also includes a flag indicating whether the user has opted to be a dater or non-dater. In the preferred embodiment, photo files are stored in a dedicated data repository, and the database only contains references to the photos.

The Server Memory 601 may include a Friends database 603, which includes a social network representing the Friend associations. In the preferred embodiment, for each user, there is one entry for each known association with another user; the entry contains the User Ids of the two users, plus a status: "confirmed", for a Friendship approved by both users; "requested", if the other user has made an unanswered request for Friendship; "pending", if the user has made an unanswered request for Friendship; or "none", if neither user has requested Friendship. In addition, each user has a single additional entry with a status of "self", which facilitates including a dater in their own Friend Group. Every time a user logs in or refreshes his/her Friend list, the system makes a call to one or more external social networking services 670 and obtains a list of the user's associates that are also users of the present application. The system then updates the Server Memory Friends database 603 as needed so that each association has one entry in the database.

The Server Memory 601 may include a Filtering Criteria database 604, containing one entry per dater that contains the dater's search constraints, such as distance, age, and gender. In a preferred embodiment, for optimization purposes, this database contains not only the search criteria, but also the complementary biographical information for each user. For example, if the database contains each dater's preferred age range, it also includes each dater's age. Thus, database searches can performed with a single database query. In other embodiments, however, the complementary biographical information may be stored in the Server Memory Users database 502. In a preferred embodiment, each entry on the Server side also contains an ordered list of daters for whom the given profile was already considered. Searches can therefore exclude previously attempted pairings.

In some embodiments, the Server Memory 601 may contain a Serve Queue database 605, a feature used in some embodiments to ensure that Evaluators receive a steady stream of profiles to evaluate. For each dater, one Serve Queue is maintained for each of the raters. The Serve Queue is a list of references to profiles that are found in searches for the dater, that need to be rated. In the preferred embodiment, User Ids are used to reference the dater, the rater, and the profile. The Serve Queue system is for optimization and is not strictly necessary.

The Server Memory 601 may contain a database of Ratings and Scores 606. In a preferred embodiment, each raw numeric rating is stored along with metadata, including the User Id of the rater, the User Id of the rated profile, and the User Id of the dater on behalf of whom the rating was performed. The database may be indexed by all three metadata. The database may also contain ancillary values based on the ratings; for example, in the preferred embodiment, the system also stores each rating mapped to a percentile rating, by means of the method of moments. In addition, the system may store in this database any other values that directly depend on the ratings, such as Scores or other useful statistics. An example of an entry in JSON may be: {evaluatorUserId: "RasEPSwH82DQ1NZdf", onBehalfOf: "P2fNb3T2Aq982Nve", profileId: "N13Mu72VhKj3Fn390Zxw", rating: 85, percentile: 90, score: {distribution: "gaussian", mean: 78.3, stddev: 11.4}

In embodiments with written evaluations, the Server Memory 601 may contain a Written Evaluations database 607. In a preferred embodiment, this database contains one entry per written evaluation, plus associated metadata including the User Id of the author, User Id of the evaluated profile, and the user Id of the dater on behalf of whom the rating was performed.

In embodiments with adaptive weighting, the Server Memory 601 may contain a Mapping Parameters database 608. In a preferred embodiment, each rater has a separate set of mapping parameters for each dater on behalf of whom he/she is rating. The mapping parameters include generally any personalized weightings, mappings, or other parameters used by the statistical processing. An example entry in JSON may be: {evaluatorUserId: "RasEPSwH82DQ1NZdf", onBehalfOf: "P2fNb3T2Aq982Nve", mean: {type: "linearVsRating", slope: 0.55, intercept: 28.8}, stddev: {type: "constant", value: 11.4}}

The Server Memory 601 may contain a Matches database 609, which stores information related to Matches. In the preferred embodiment, each Match is represented by two entries: one for each dater, with a reference to the other dater via his/her User Id. Any additional information regarding Matches, such as feedback on a Match, or whether a Match was viewed, may be stored in one or both entries as well.

In embodiments with a chat feature, the Server Memory 601 may contain a Conversations database 610, which contains messages sent between users, as well as metadata including the User Id of the author, the User Id(s) of the intended recipient(s), and a timestamp. In the preferred embodiment, each conversation is referenced by a unique Conversation Id; the database may also contain a directory of each user's conversations, referenced by the Conversation Id.

The Server Memory 601 may contain a User Activity database 611, which contains data concerning each user's activity on the application. In the preferred embodiment, there is one entry per user, and the entry contains a timestamp of the user's last activity on the application. This information may be displayed on the user's profile formatted as "last online 10 minutes ago," for example. This information may also be used to determine which users are available to solicit for ratings.

The Server Program 621 has several functions. One function of the Server Program 621 is to sync 622 the Server Memory 601 and the Client Memory 501. The preferred embodiment uses the DDP protocol, in which the Server Program 621 and a Client Program 521 may issue each other "added," "changed," and "removed" directives over the internet 660, which instruct the other to add, edit, or delete a specified entry. On the Server side, the Server Program 621 keeps a log of all users who are actively using the application, and a reference to all database queries that were used to publish data. The Server Program 621 monitors when any data changes that would affect an active query, which may be performed efficiently through oplog tailing, for example. When a change occurs, the Server Program 621 identifies the client devices affected by the change, and issues a DDP directive to the appropriate Client Program(s) 521, each of which updates its Client Memory 501 accordingly. Conversely, when the Server Program 621 receives a DDP message from a Client Device, the Server Program 621 must first verify and validate the data received. If the user in question has access to make the requested change to the database, and the data is valid, then the Server Program 621 makes the change in the Server Memory 601. In such a way, the various Client Devices may communicate via the Server acting as a go-between. Other embodiments may use different methods to handle the data storage, updating, or communication.

Another function of the Server Program 621 is to store new user information and validate existing user information 623. In the preferred embodiment, the Client Program 521 first validates a user's identity using a external social networking service 670; it receives an access token from the social networking service, and sends the access token encrypted to the Server Program 621. The Server verifies the validity of the access token with the external social networking service, utilizing an "app secret" string to ensure the validity of the transaction. The Server Program 621 may also receive from the external social networking service 670 basic autobiographical information including the user's name, age, gender, etc. Once a user is verified, if the user already exists in the Server Memory Users database 602, then the user is regarded as an existing user; otherwise, the Server Program 621 stores the information as a new entry and assigns the user a unique User Id. The Server Program 621 then syncs the Client Memory 501 to match the pertinent entry in the Server Memory 601.

Another function of the Server Program 621 is to validate and store profile information 625. After a user has edited their profile, the Server Program 621 receives the updates from the Client Program 521. First, the Server Program 621 validates the data, for example by cross-checking the supplied information against an external social networking service 670. As a security feature against hackers uploading illicit photographs, the Server Program 621 only receives from the Client Program 521 metadata about the photo: the source social networking service or social media service 670, the unique identifier for the photograph, and the cropping parameters. The Server Program 521 then downloads the photo independently from the client, crops the photo itself, and stores the photo in the Server Memory Users database 602. In some embodiments, Friends may be solicited to vouch for the data supplied.

Another function of the Server Program 621 is to store a user's choice to be a dater or a non-dater 626, in which case they may only rate for Friends. This choice may be stored in the Server Memory Users database under the user's entry. The Server Program 621 may also add or remove the user from the Server Memory Filtering Criteria database 604. If a former dater opts to be a non-dater, the Server Program 621 may also take other appropriate steps such as removing or flagging entries in the Server Memory Matches database 609 for which the user was one of the Matched parties, so that the user does not appear as a dater on the application and is excluded from romantic activities on the application.

Another function of the Server Program 621 is to store filtering criteria 627 specified by a user into the Server Memory Filtering Criteria database 604. In the preferred embodiment, the Server Program 621 immediately re-runs the search with the new filtering criteria, and removes any excluded profiles from the Serve Queues of the user and the user's Friends.

Another function of the Server Program 621 is to search for dater pairs satisfying mutual filtering criteria 628. In the preferred embodiment, the dating pool is narrowed through search criteria including an age range, gender preference, and distance. The search looks for other daters with mutually satisfied filtering criteria. In the preferred embodiment, the Server Memory Filtering Criteria database 604 contains both the criteria (e.g. age range) and the corresponding autobiographical data (e.g. age) of each dater. Therefore, the search is a single database query. For example, suppose the search is being performed for a female 25-year-old dater looking for a male in the age range 21-29. Then the corresponding search subset would look for entries of daters: 1. who are male, 2. whose preferred gender includes female, 3. whose age is in the range 21-29, and 4. whose preferred age range includes 25. In the preferred embodiment, the search criteria also includes distance.

Another function of the Server Program 621 is to relay Friend requests 629 between users. When a user chooses to request a Friendship, the Server Program 621 makes changes to the two corresponding entries in the Server Program Friends database 603. The Server Program 621 edits the entry belonging to the requesting user corresponding to the requested user, changing the status from "none" to "pending." Similarly, the Server Program 621 edits the entry belonging to the requested user corresponding to the requesting user, changing the status from "none" to "requested." The changes are propagated to both users' Client Memory Friend database 603, and the status changes are reflected on the Friend listings on each user's UI. The requested Friend may either confirm or deny the Friend request. If confirmed, the Server Program 621 changes both entries' status to "confirmed," and if denied, the Server Program 621 changes both entries' status back to "none." At any point, if a confirmed Friend cancels a Friendship, the Server Program 621 changes the status of the Friend entries to "none" for both Friends.

In the preferred embodiment, the system uses prior information in determining whether a pairing warrants a Match. Prior information is any information, such as dater preferences, known to the system before ratings are collected. In such cases, another function of the Server Program 621 is to initialize a Group Unidirectional Score and Bidirectional Score 630. These Scores are initialized based on prior information after two users are first considered as a pairing. One Group Unidirectional Score is assigned to each dater, and represents the system's belief in how the dater feels about the other dater. This Score may be based on historical ratings and outcomes of each dater, and of each dater by users system-wide. These two Group Unidirectional Scores may be combined using a combination function to assign a prior Overall Bidirectional Score, which represents the system's belief in how compatible the two daters would be together. In some embodiments, a prior Overall Bidirectional Score may be computed directly. This Score may be used by the system to determine a priority for the pairing compared to other pairings involving one of the daters.

In embodiments that use a Serve Queue feature to buffer profiles, another function of the Server Program 621 is to restock a user's Serve Queue 631. If the user is a dater, the Serve Queue may contain profiles intended as suggested pairings with the user. If the user is Friend, the Serve Queue may contain profiles intended as suggested pairings with the Friend's Friend. If the user is a matchmaker, the Serve Queue may contain pairings of daters not known to the user. In any case, Serve Queues are a solution to ensure that a rater always has profiles or pairings to rate if possible in order to keep the user engaged. The Server Program 621 may perform this function at the request of a Client Program 521, or may itself monitor when one of a client's Serve Queues needs restocking. In the preferred embodiment, the Server Program's 621 first resort is to fill the Serve Queue with profiles or pairings that have already been found by a search 628 and assigned Scores 630, 638 that indicate a high priority. Otherwise, as a second resort, the system may schedule a new search 628. In order to actually perform the restocking, the Serve Queue adds one or more entries to the Server Memory Serve Queue database 605, each entry containing the User Ids of both daters constituting the proposed pairing.

Another function of the Server Program 621 is to collate and send profile data 632 to appropriate client devices. In the preferred embodiment, any Client Program 521 may request one or more specific profiles from the Server Program 621, by referencing the User Id corresponding to the profile; however, the Server Program 621 may preemptively send profiles too, for example at the same time as adding an entry to a user's Serve Queue. The Server Program 621 verifies that the requesting user should have access to the requested profile. If so, then the Server Program 621 collates all the information that goes into a displayed profile, including: photos and biographical information in the Server Memory Users database 602; raw ratings of the profile made by Friends, from the Server Memory Ratings and Scores database 606; written evaluations of the profile made by Friends, from the Server Memory Written Evaluations database 607; the distance between the two daters, based on information in the Server Memory User Activity database 611; and, how much time has elapsed since the user was last active, from the Server Memory User Activity database 611. The Server Program 621 may have different tiers of privacy depending on the relationship of the requesting user with the user of the requested profile.

In embodiments with written evaluations, another function of the Server Program 621 is to store a written evaluation 633. In the preferred embodiment, a written evaluation may be optionally supplied by a user when viewing a profile, in addition to supplying a numeric rating. The Server Program 621 stores the content of the evaluation in the Written Evaluations database 607, along with metadata including: the User Id of the author, the User Id of the dater in the profile, and the User Id of the Friend on behalf of whom the evaluation was performed. When another user is presented with the same profile to rate on behalf of the same Friend, the system sends the written evaluation to be displayed with the profile 532.

Another function of the Server Program 621 is to store a rating 634 made by a user. When the Server Program receives the rating from a Client Program 521, it stores the numeric rating in the Server Memory Ratings and Scores database 606. If the rating is made on behalf of a Friend, the Server Program 621 stores the rating along with metadata including: the User Id of the rater, the User Id of the dater in the profile, and the User Id of the Friend on behalf of whom the evaluation was performed. If the rating is made by a matchmaker, the Server Program 621 stores the rating along with metadata including: the User Id of the rater, and the User Ids of the two daters in the pairing. In the preferred embodiment, the Server Program 621 also maps the rating to a percentile rating in comparison to the rater's previous ratings performed in the same role (i.e., on behalf of the same Friend, or as matchmaker), using the method of moments. Also, the Server Program 621 uses the personalized mapping parameters for the rater to calculate a Score. A list of Scores for each pairing is also stored in the Server Memory Ratings and Scores database 606. In the preferred embodiment, a rating signifies that the rater is done with the profile for the moment, and the Server Program 621 may remove the reference to the profile from the appropriate Serve Queue in the Server Memory Serve Queue database 605.

Another function of the Server Program 621 is to determine and issue a match 635. The Server Program has criteria to determine if a pairing of two daters constitutes a match, primarily based on ratings received from users, which may include: one or both of the daters, one or more of the daters' Friends, and one or more matchmakers. In the preferred embodiment, a necessary but not sufficient condition for a pairing to warrant a Match is that the pairing has an Overall Bidirectional Score that indicates a high probability for a successful Match; for example, the embodiment may specify a minimum probability that the bidirectional outcome will be above a specified percentile. The Server Program 621 may also consider the number of recent Matches each user has received, attempting to give each dater a sufficient but not overwhelming number. The Server Program 621 may prioritize users whose actions indicate they are seriously pursuing a relationship. Some embodiments may rely less on the calculated Scores, and may consider other traits indicating compatibility, such as users with similar or complementary personality types, users with similar schedules, users with compatible conversation level, users with similar relationship goals, users with similar interests, etc. In any case, once a Match is identified, the Server Program 621 notifies or schedules a notification to each dater's Client Program 521. In the preferred embodiment, the Server Program inserts two entries, one for each dater, into the Server Memory Matches database 609. The entry contains the User Id of the other dater, a timestamp, and any other information pertaining to that particular Match. The Server Program then syncs the update to the daters' Client Programs at the next opportunity 622.

In embodiments that use feedback to inform future Matching, another function of the Server Program is to gather feedback on a Match 636. In the preferred embodiment, the Server Program 621 coordinates the gathering of feedback about a Match from the two daters, their Friends, and those users' client devices 536. The Server Program 621 may attempt to gather unidirectional feedback—how one dater feels about another, as well as bidirectional feedback—the quality of the pairing. This information is collected in the Server Memory Matches database 609, but kept private from the users involved.

In embodiments with adaptive weighting of ratings, another function of the Server Program 621 is to calculate weighting or mapping parameters 637. In some embodiments, a linear weighting is calculated for each rater, possibly on a per-dater basis. When feedback arrives on a Match, the Server Program 621 examines each rating on that Match, and increases/decreases the weighting of the rater if the rater was accurate/inaccurate in predicting the outcome. The system may also increase/decrease the weighting of a rater if the rater agrees/differs from another rater on the same rating, especially when the other rater is the dater in question. In the preferred embodiment, ratings are mapped to a Score (probability distribution) via a set of personalized mapping parameters. These parameters are continually updated based on new information (see FIGS. 3-4).

In the preferred embodiment, another function of the Server Program 621 is to update Scores 638, as previously described in FIGS. 3-4. A Score may be updated based on the Server Program's receiving a new rating 634, or based on a recalculation of personalized weighting or mapping parameters 637. When any Score is updated, the Server Program 621 also updates any dependencies. In some embodiments, the system may recalculate mapping parameters 637 concurrently with updating Scores 638, incorporating any newly received ratings into the optimization process.

In embodiments with a chat feature, another function of the Server Program 621 is to store and relay messages 639. In the preferred embodiment, when a user messages another user, the Client Program 521 sends the data to the Server Program 621, which first checks that the user is allowed to message the intended recipient. The Server Program 621 then ensures that the message has a correct timestamp, and stores the message in the Server Memory Conversations database 610, ensuring that the intended recipient will receive the message at the next available opportunity. In some embodiments, the chat feature may be text-, audio-, or video-based.

FIG. 7 shows an example of an evaluation page 700 of a client interface of an embodiment. The evaluation page 700 is made up of a number of buttons, icons, images, and other elements. They include a "change dater" button 715 that shows the currently selected dater 715 and allows the user to select a different dater. For the purpose of this example, the dater selected 715, named Dominic, is the user. In other words, the user is evaluating profiles on his own behalf. Dominic 715 could use the "change dater" button 715 to select a different dater to evaluate profiles on behalf of.

The evaluation page 700 also includes a "menu" button 740 that opens a series of other screens (not shown) for the user, a "chat" button 730 that opens a communication tool (not shown), a "more" button 750 that takes the user to a menu (not shown) of additional options and actions pertaining to the displayed profile or pairing, and an input mechanism 720 for the user to provide an evaluation. In this case, the input mechanism 720 is a slider bar.

The evaluation page 700 also includes a profile image of another user 710 named Jennifer along with various information about that user. The fact that Jennifer's profile information and image 710 is shown here means that Jennifer, like Dominic, is a dater.

When the user inputs an evaluation, the system stores the evaluation and displays another profile for the user to evaluate on behalf of the currently selected dater 715.

As stated above, the dater currently selected 715, Dominic, is the user of the evaluation page 700 in this example. Dominic is evaluating profiles for himself. He has not yet evaluated Jennifer's profile. Images of two of Dominic's Friends 725 appear below the slider bar 720. These two images 725 represent previous evaluations (ratings) by these Friends on Dominic's behalf of whether or not Jennifer would be a good match for Dominic. In this case, both Friends have given Jennifer's profile a positive evaluation. In other words, both Friends believe Jennifer and Dominic would be a good fit for one another, and stand a good chance of becoming a Match. In addition to a positive evaluation, one Friend also left a written evaluation (comment) 760 to express his enthusiasm for the pairing of Jennifer and Dominic. Dominic's Friends 725 may or may not be Friends with each other. In some embodiments, the Friend's ratings may be visible to each other, but only if they are Friends with each other.

Since Jennifer is a dater (like Dominic), Jennifer may have Friends (not shown) who may evaluate profiles on her behalf. Jennifer also may not have Friends; it is not shown from Dominic's point of view, and Jennifer may use the evaluation page of her client interface (not shown) on her own behalf whether or not she has Friends. Jennifer and any Friends evaluating profiles on her behalf may at some point be shown Dominic's profile and asked to evaluate his potential for a successful pairing with Jennifer.

The images of Dominic's Friends 725 below the slider bar 720 double as buttons. Tapping on one of these buttons 725 will take the user (Dominic) to a chat with that Friend, and provide the user with a means of focusing the discussion on the profile the Friend evaluated, whom the user is currently in the process of evaluating.

Continuing with the example, suppose Dominic taps the Friend image 725 on the left. See FIG. 8, where the rest of this example is continued.

FIG. 8 shows a chat page 800 of a client interface of an embodiment. The chat page 800 is made up of a number of buttons, icons, images, and other elements. They include a "back" button 820 that returns the user to the last screen viewed, as well as a "more" button 825 that takes the user to a menu (not shown) of additional options and actions.

The chat page 800 includes a text input box 830. At times, the chat page 800 may display a keyboard 832 with which the user may type messages. A "send" button 834 is positioned next to the text input box. Tapping the send button sends a message.

Messages are displayed in the chat window 810. Messages from the user 840 are aligned to the right. Messages from a different user 842 are aligned to the left. Messages and notifications from the system 844 appear in the center. The chat page 800 includes an image 846 that shows the user with whom the present user is engaged in chat. In some embodiments the image 846 is clickable and directs the user to a Friend page that gives a synopsis of the two Friends' history together in the application.

Continuing with the example from FIG. 7, the user (Dominic) is chatting with another user named Alan. Dominic and Alan are Friends. Per the example from FIG. 7, Dominic has arrived at the present chat page 800 by tapping on the Friend image indicating Alan 725 below the slider bar 720. Such an action directs Domic to the present chat page 800. It is possible for a user to arrive at the chat page 800 by other means. The action of Dominic tapping the Friend image of Alan 725 also causes an image of Jennifer 850 to be included in the text input box 830. This assists Dominic in chatting with Alan about Jennifer; Alan can quickly reference who Jennifer is. When Dominic sends the message currently in the text box 830, tapping on the image of Jennifer 850 will link to Jennifer's profile, allowing both Alan and Dominic to take another look at her information (the same is true of Jane 860). This ability to quickly reference and refresh information about daters allows for efficient, focused communication between Friends.

FIG. 9 shows an example of a matchmaker's evaluation page 900 of a client interface of an embodiment. The evaluation page 900 is made up of a number of buttons, icons, images, and other elements. The evaluation page 900 includes a "menu" button 940 that opens a series of other screens (not shown) for the user, a "chat" button 930 that opens a communication tool (not shown), a "more" button 950 that takes the user to a menu (not shown) of additional options and actions, and an input mechanism 920 for the user to provide an evaluation. In this case, the input mechanism 920 is a slider bar.

In this example, the user is evaluating a pairing of two daters 970, 960. The user is not either of the daters 970, 960. Instead, the user is a matchmaker. In some embodiments, the matchmaker can switch between each dater's profile information by clicking on the dater's photograph or name. Depending on the embodiment, a matchmaker may be Friends with one dater, both daters, or neither dater. In some embodiments, the matchmaker may be able to see prior evaluations from one dater's Friends. In other embodiments, the matchmaker may be able to see prior evaluations from both dater's Friends. In other embodiments, the matchmaker may be able to see prior evaluations from other matchmakers. In other embodiments, the matchmaker may be able to see a selection or combination of these prior evaluations. In other embodiments, the matchmaker may not be able to see any prior evaluations.

When the matchmaker inputs an evaluation, the system stores the evaluation and displays another pairing for the matchmaker to evaluate, or may switch to rating single profiles on behalf of a Friend. Depending on the embodiment, the pairing may be of two new daters, or of the one of the same daters from a previous pairing with a new dater. In some embodiments, the pairing may include profiles of people who are not users.

FIG. 10 shows an example of a suggesting page 1000 of a client interface of an embodiment. The suggesting page 1000 is made up of a number of buttons, icons, images, and other elements. The suggesting page 1000 includes a "menu" button 1040 that opens a series of other screens (not shown) for the user, as well as a "chat" button 1030 that opens a communication tool (not shown).

The suggesting page 1000 allows the user to input a preliminary evaluation (in this embodiment, a yes vote) 1020, and the profile or pairing may then be evaluated further at a later time. Profiles are displayed as tabs in a vertical scroll 1020, and include various information about the associated dater.

A "suggest" button 1050 is visible to the right of every profile tab. Tapping this button 1050 allows the user to provide a simple "yes" evaluation to a profile or pairing. The system stores the suggestion, which constitutes a type of binary rating, and may be mapped by the system into an Individual Unidirectional Score.

The suggesting page 1000 may include a search feature. In this example, it is a search bar 1010. The user may use the search bar 1010 to search for daters who are not displayed in the scroll 1020. The user may also use the search bar 1010 to search for keywords or tags, including but not limited to interests, hobbies, location information like a city and/or zip code, an age range, job, school, nationality, and so on.

Other embodiments combine various aspects of the aforementioned embodiments, as well as various additional aspects in keeping with the spirit of the invention. In general, the invention can be applied to any situation involving social and romantic connections in a context where peer input and analysis, and in which users contribute to a better understanding of other people such that a suggestion, evaluation, or introduction may be made on their behalf.

While the present invention has been described in terms of a system implemented over a public network, such as the internet, methods of the present invention can also be implemented over a private network and even without a network.

The invention claimed is:

1. A method of electronically evaluating a potential romantic pairing
    of daters, wherein the method comprises:
    selecting one or more evaluators;
    collecting and recording evaluations from the one or more evaluators, wherein
    each of the evaluations is one of an opinion by one evaluator on a quality of
    the potential romantic pairing or suitability of one of the daters for the other;
    recording a history of the evaluations;
    recording at least one evaluator-dater relationship;
    calculating a score representing the quality of the potential romantic pairing or suitability of one of the daters for the other, wherein calculation of the score is based on the history of the evaluations and the evaluator-dater relationship;
    calculating a certainty of the score, wherein calculation of the certainty of the score is determined by a number of evaluations received and the evaluator-dater relationship;
    wherein if the certainty of the score is below a predetermined threshold, collecting and recording one or more additional evaluations; and
    wherein if the certainty of the score and the score satisfy a predetermined condition indicating a high certainty of the potential romantic pairing being high quality, issuing a match between daters, wherein the matched daters are connected by a system and invited to communicate.

2. The method of claim 1, wherein the score and the certainty of the
    score are defined by a set of numbers that parametrize a probability
    distribution.

3. An electronic system for evaluating the potential romantic pairing of
    two daters, wherein the system comprises:
    a memory comprising:
        a record of user profile information;
        a record of evaluations by users;
        a record of relationships between users; and
        a record of matches issued by the system;
    a program, wherein the functions comprise:
        selecting one or more evaluators;
        collecting and recording evaluations from the one or more evaluators,
        wherein each of the evaluations is one of an opinion by one evaluator on a
        quality of the potential romantic pairing or suitability of one of the daters
        for the other;
        recording a history of evaluations;
        recording at least one evaluator-dater relationship;
        calculating a score representing the quality of the potential romantic
        pairing or suitability of one of the daters for the other;
        wherein the calculation of the score is based on the history of evaluations
        and the evaluator-dater relationship;
        calculating a certainty of the score, wherein calculation of the certainty of the score is determined by a number of evaluations received and the evaluator-dater relationship;
        wherein if the certainty of the score is below a predetermined threshold, collecting and recording one or more additional evaluations; and
        wherein if the certainty of the score and the score satisfy a predetermined condition indicating a high certainty of the potential romantic pairing being high quality, issuing a match between daters, wherein the matched daters are connected by the system and invited to communicate.

4. The electronic system of claim 3, wherein the score and the certainty
    of the score are defined by a set of numbers that parametrize a probability
    distribution.

5. A non-transitory computer readable medium that stores a set of
    instructions that is executable by at least one processor of an electronic system
    to cause the electronic system to perform a method of electronically
    evaluating a potential romantic pairing of daters, the method comprising:
    selecting one or more evaluators;
    collecting and recording evaluations from the one or more evaluators, wherein
    each of the evaluations is one of an opinion by one evaluator on a quality of
    the potential romantic pairing or suitability of one of the daters for the other;
    recording a history of the evaluations;
    recording at least one evaluator-dater relationship;
    calculating a score representing the quality of the potential romantic pairing or suitability of one of the daters for the other, wherein calculation of the score is based on the history of the evaluations and the evaluator-dater relationship;

calculating a certainty of the score, wherein calculation of the certainty of the score is determined by a number of evaluations received and the evaluator-dater relationship;

wherein if the certainty of the score is below a predetermined threshold, collecting and recording one or more additional evaluations; and wherein if the certainty of the score and the score satisfy a predetermined condition indicating a high certainty of the potential romantic pairing being high quality, issuing a match between daters, wherein the matched daters are connected by a system and invited to communicate.

6. The non-transitory computer readable medium of claim 5, wherein the score and the certainty of the score are defined by a set of numbers that parametrize a probability distribution.

\* \* \* \* \*